US008168393B2

(12) United States Patent
Goldstein et al.

(10) Patent No.: US 8,168,393 B2
(45) Date of Patent: May 1, 2012

(54) COMPOSITIONS AND METHODS FOR DIAGNOSING TUMORS USING LEDGF/P75

(75) Inventors: Lee E. Goldstein, Newton, MA (US); Ling Fu, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 706 days.

(21) Appl. No.: 12/070,039

(22) Filed: Feb. 13, 2008

(65) Prior Publication Data
US 2009/0053712 A1 Feb. 26, 2009

Related U.S. Application Data

(60) Provisional application No. 60/901,740, filed on Feb. 16, 2007.

(51) Int. Cl.
*G01N 33/53* (2006.01)
(52) U.S. Cl. .............................. 435/7.1; 435/4; 530/350
(58) Field of Classification Search .................. None
See application file for complete search history.

(56) References Cited

U.S. PATENT DOCUMENTS

| | | | |
|---|---|---|---|
| 6,699,967 B1 | 3/2004 | Burgess et al. | |
| 6,750,052 B1 | 6/2004 | Shinohara et al. | |
| 2002/0155119 A1 | 10/2002 | Sikes et al. | |
| 2003/0008330 A1 | 1/2003 | Abe et al. | |
| 2003/0059868 A1 | 3/2003 | Greenwood et al. | |
| 2003/0105594 A1 | 6/2003 | Westbrook et al. | |
| 2003/0190708 A1 | 10/2003 | Burgess et al. | |
| 2003/0215875 A1 | 11/2003 | Tan et al. | |
| 2004/0038348 A1 | 2/2004 | Pena et al. | |
| 2004/0087505 A1 | 5/2004 | Pena et al. | |
| 2004/0091487 A1 | 5/2004 | Kalpana | |
| 2004/0142333 A1 | 7/2004 | Lu et al. | |

FOREIGN PATENT DOCUMENTS

| | | |
|---|---|---|
| EP | 0 438 520 B1 | 7/1991 |
| WO | WO 90/07380 | 7/1990 |
| WO | WO 96/26782 | 9/1996 |
| WO | WO 00/29578 A1 | 5/2000 |
| WO | WO 2005/005601 A2 | 1/2005 |
| WO | WO 2005/015236 A2 | 2/2005 |

OTHER PUBLICATIONS

Daugaard et al. (2007). Lens epithelium-derived growth factor is an Hsp70-2 regulated guardian of lysosomal stability in human cancer. Cancer. Res. 67(6):2559-2567.*
Shnaper et al. (2009). Elevated levels of MIC-1/GDF15 in the cerebrospinal fluid patients are associated with glioblastoma and worse outcome. Int. J. Cancer. 125:2624-2630.*
Casiano et al., "Tumor-associated antigen arrays for the serological diagnosis of cancer", *Mol. Cell.Proteomics*, 5(10):1745-1759 (2006).
Bernier et al., "Characterization of the subventricular zone of the adult human brain: evidence for the involvement of Bcl-2", *Neurosci. Res.*, 37(1):67-78 (2000).

Bonni et al., "Regulation of Gliogenesis in the Central Nervous System by the JAK-STAT Signaling Pathway", *Science*, 278:477-483 (1997).
Buc-Caron, M.H., "Neuroepithelial progenitor cells explanted from human fetal brain proliferate and differentiate in vitro", *Neurobiol. Dis.*, 2:37-47 (1995).
Busschots et al., "The Interaction of LEDGF/p75 with Integrase is Lentivirus-specific and Promotes DNA Binding", *J. Biol. Chem.*, 280(18):17841-17847 (2005).
Chylack et al., "Lens epithelium-derived growth factor (LEDGF/p75) expression in fetal and adult human brain", *Exp. Eye Res.*, 79:941-948 (2004).
Crino et al., "Presence and phosphorylation of transcription factors in developing dendrites", *Proc. Natl. Acad. Sci. USA*, 95:2313-2318 (1998).
Daniels et al., "Antinuclear Autoantibodies in Prostate Cancer: Immunity to LEDGF/p75, a Survival Protein Highly Expressed in Prostate Tumors and Cleaved During Apoptosis", *Prostate*, 62:14-26 (2005).
Dietz et al., "The family of hepatoma-derived growth factor proteins: characterization of a new member HRP-4 and classification of its subfamilies", *Biochem. J.*, 366:491-500 (2002).
Emiliani et al., "Integrase Mutants Defective for Interaction with LEDGF/p75 Are Impaired in Chromosome Tethering and HIV-1 Replication", *J. Biol. Chem.*, 280(27):25517-25523 (2005).
Eriksson et al., "Neurogenesis in the adult human hippocampus", *Nat. Med.*, 4(11):1313-1317 (1998).
Fatma et al., "Transcriptional Regulation of the Antioxidant Protein 2 Gene, a Thiol-specific Antioxidant, by Lens Epithelium-derived Growth Factor to Protect Cells from Oxidative Stress", *J. Biol. Chem.*, 276(52):48899-48907 (2001).
Fujioka et al., "Activation of cAMP Signaling Facilitates the Morphological Maturation of Newborn Neurons in Adult Hippocampus", *J. Neurosci.*, 24(2):319-328 (2004).
Ge et al., "Isolation of cDNAs encoding novel transcription coactivators p52 and p75 reveals an alternate regulatory mechanism of transcriptional activation", *Embo J.*, 17(22):6723-6729 (1998).

(Continued)

*Primary Examiner* — Christine J Saoud
*Assistant Examiner* — Jon M Lockard
(74) *Attorney, Agent, or Firm* — Mintz Levin Cohn Ferris Glovsky and Popeo, P.C.; Ingrid A. Beattie

(57) ABSTRACT

The invention provides methods for diagnosing tumors in mammals using a reagent that bind to LEDGF/p75 or to a nucleic acid encoding LEDGF/p75. For example, the tumor may be located in the CNS, the prostate, the skin, the bone marrow, or the gut of the mammal. Also provided are methods for diagnosing brain tumors such as medulloblastomas, meningiomas, astrocytomas, glioblastomas multiforme, and ependymomas by examining LEDGF/p75 or a nucleic acid encoding LEDGF/p75 localization. The invention also involves methods for diagnosing cancers involving cancerous epithelial cells such as colon cancer. The instant invention also provides methods for isolating stem cells from a heterogeneous population of cells, as well as methods for identifying neuroepithelial stem cells, newly differentiated neurons, and astrocytes in a subject. Also provided are methods for inducing the differentiation of neuroepithelial stem cells into astrocytes or neurons and methods for screening candidate compounds that regulate the differentiation of neuroepithelial stem cells.

3 Claims, 12 Drawing Sheets

OTHER PUBLICATIONS

GenBank Accession No. AAC25167, Mar. 23, 2001.
GenBank Accession No. AAF25870, Jul. 31, 2002.
GenBank Accession No. AAF25871, Jul. 31, 2002.
GenBank Accession No. AF098482, Dec. 23, 1998.
GenBank GeneID:11168, updated Feb. 3, 2008.
Giachino et al., "cAMP Response Element-Binding Protein Regulates Differentiation and Survival of Newborn Neurons in the Olfactory Bulb", *J. Neurosci.*, 25(44):10105-10118 (2005).
Goldstein et al., "Alzheimer's Disease β-Amyloid (Aβ) in the Lens: Interactions with AlphaB-Crystallin, Small Heat Schock Proteins, and Redox-Active Metal", *Invest. Ophthalmol. Vis. Sci.*, 45:3507 (2004) (Abstract Only).
Goldstein et al., "Beta-Amyloid Promotes Lens Protein Aggregation and is Associated with Supranuclear Lens Opacification", *Invest. Ophthalmol. Vis. Sci.*, 43 (2002) (Abstract Only).
Goldstein et al., "Expression and Further Characterization of Alzheimer's Disease Beta-amyloid (Abeta) in Human Aqueous Humor and Lens", *Invest. Ophthalmol. Vis. Sci.*, Abstract No. 3488-B191 (2003).
Goldstein et al., "Lens Epithelium-Derived Growth Factor (LEDGF) in the Retina and Brain", *Invest. Ophthalmol. Vis. Sci.*, 41(4):S870, Abstract No. 4626-B573 (2000).
Hussey et al., "Fusion of the *NUP98* gene with the *LEDGF/p52* gene defines a recurrent acute myeloid leukemia translocation", *BMC Genetics*, 2:20-23 (2001).
Johe et al., "Single factors direct the differentiation of stem cells from the fetal and adult central nervous system", *Genes Dev.*, 10:3129-3140 (1996).
Kirschenbaum et al., "In vitro Neuronal Production and Differentiation by Precursor Cells Derived from the Adult Human Forebrain", *Cereb. Cortex*, 4(6):576-589 (1994).
Kubo et al., "Cellular distribution of lens epithelium-derived growth factor (LEDGF) in the rat eye: loss of LEDGF from nuclei of differentiating cells", *Histochem. Cell Biol.*, 119:289-299 (2003).
Lepourcelet et al., "Insights into developmental mechanisms and cancers in the mammalian intestine derived from serial analysis of gene expression and study of the hepatoma-derived growth factor (HDGF)", *Develop. Dis.*, 32(2):415-427 (2005).
Llano et al., "LEDGF/p75 Determines Cellular Trafficking of Diverse Lentiviral but Not Murine Oncoretroviral Integrase Proteins and Is a Component of Functional Lentiviral Preintegration Complexes", *J. Virol.*, 78(17):9524-9537 (2004).
Llano et al., "Lens Epithelium-derived Growth Factor/p75 Prevents Proteasomal Degradation of HIV-1 Integrase", *J. Biol. Chem.*, 279(53):55570-55577 (2004).
Lonze et al., "Function and Regulation of CREB Family Transcription Factors in the Nervous System", *Neuron*, 35:605-623 (2002).
Maertens et al., "Identification and Characterization of a Functional Nuclear Localization Signal in the HIV-1 Integrase Interactor LEDGF/p75", *J. Biol. Chem.*, 279(32):33421-33429 (2004).
Maertens et al., "Measuring protein-protein interactions inside living cells using single color fluorescence correlation spectroscopy. Application to human immunodeficiency virus type 1 integrase and LEDGF/p75", *FASEB J.*, 19(8):1039-1041 (2005).
Monti et al., "NMDA receptor-dependent CREB activation in survival of cerebellar granule cells during in vivo and in vitro development", *Eur. J. Neurosci.*, 16:1490-1498 (2002).
Murphy et al., "Morphological plasticity of dendritic spines in central neurons is mediated by activation of cAMP response element binding protein", *Proc. Natl. Acad. Sci. USA*, 94:1482-1487 (1997).
Nakagawa et al., "Regulation of Neurogenesis in Adult Mouse Hippocampus by cAMP and the cAMP Response Element-Binding Protein", *J. Neurosci.*, 22(9):3673-3682 (2002).
Pons et al., "Vitronectin regulates Sonic hedgehog activity during cerebellum development through CREB phosphorylation", *Development*, 128:1481-1492 (2001).
Redmond et al., "Calcium Regulation of Dendritic Growth via CaM Kinase IV and CREB-Mediated Transcription", *Neuron*, 34:999-1010 (2002).
Riccio et al., "Mediation by a CREB Family Transcription Factor of NGF-Dependent Survival of Sympathetic Neurons", *Science*, 286:2358-2361 (1999).
Rubinson et al., "A lentivirus-based system to functionally silence genes in primary mammalian cells, stem cells and transgenic mice by RNA interference", *Nat. Genet.*, 33(3):401-406 (2003).
Singh et al., "LEDGF Binds to Heat Shock and Stress-Related Element to Activate the Expression of Stress-Related Genes", *Biochem. Biophys. Res. Commun.*, 283:943-955 (2001).
Singh et al., "Lens Epithelium-Derived Growth Factor: Effects on Growth and Survival of Lens Epithelial Cells, Keratinocytes, and Fibroblasts", *Biochem. Biophys. Res. Commun.*, 267:373-381 (2000).
Singh et al., "Lens Epithemlium-Derived Growth Factor: Increased Resistance to Thermal and Oxidative Stresses", *Invest. Ophthalmol. Vis. Sci.*, 40(7):1444-1451 (1999).
Vanegas et al., "Identification of the LEDGF/p75 HIV-1 integrase-interaction domain and NLS reveals NLS-independent chromatin tethering", *J. Cell Sci.*, 118(Pt. 8):1733-1743 (2005).
Walton et al., "CREB Phosphorylation Promotes Nerve Cell Survival", *J. Neurochem.*, 73(5):1836-1842 (1999).
Walton et al., "Immediate Early Gene Transcription and Synaptic Modulation", *J. Neurosci. Res.*, 58(1):96-106 (1999).
Fu et al., "Differential Expression of Lens Epithelial-derived Growth Factor (LEDGF) During Neuroepithelial Stem Cell Differentiation in The CNS", *ARVO Meeting Abstracts*, 45:1719 (May 1, 2004) (Abstract Only).
Goldstein et al., "Lens Epithelium-Derived Growth Factor (LEDGF) in the Retina and Brain", *ARVO/IOVS*, 41(4):4626-B573 (2000) (Abstract Only).
Mancini et al., "Lens Epithelial-Derived Growth Factor (LEDGF) is Expressed in Neurons Within the Mammalian Central Nervous System", *Invest. Ophthalmol. Vis. Sci.*, 44:E-Abstract 4509 (2003) (Abstract Only).
Mancini et al., "Lens epithelial-derived growth factor (LEDGF) is differentially expressed and localized in mammalian neuroepithelial stem cells, neurons and astrocytes", *Soc. Neurosci. Abstract Archive*, 333.11 (2003) (Abstract Only).

* cited by examiner

Goldstein

Goldstein

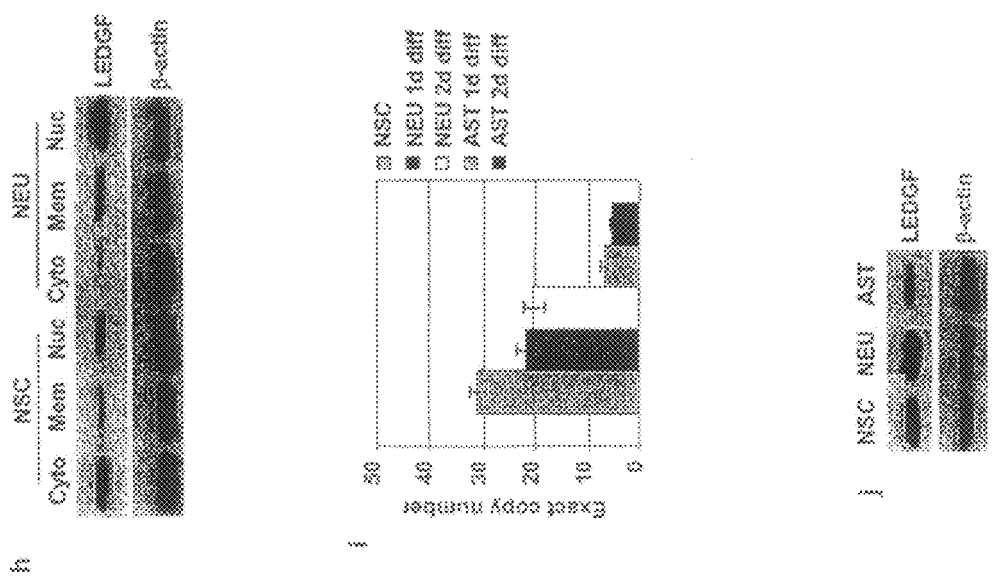

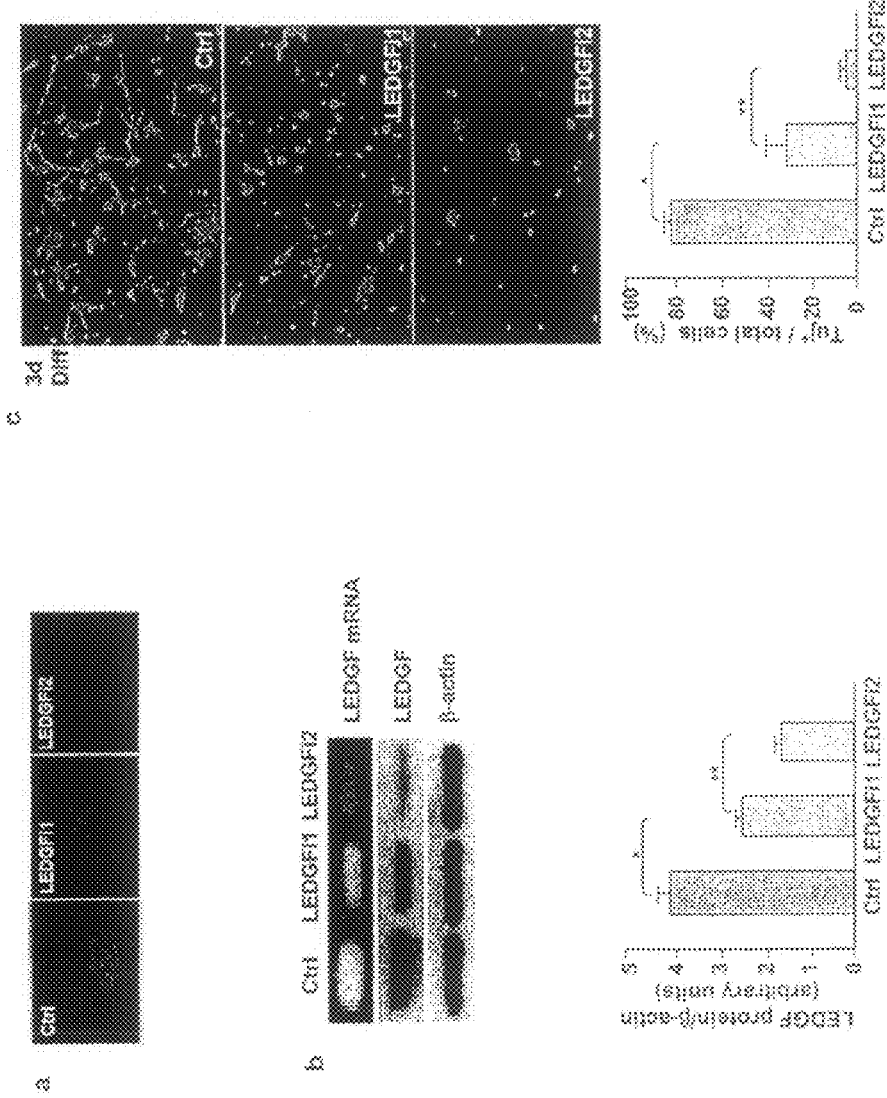

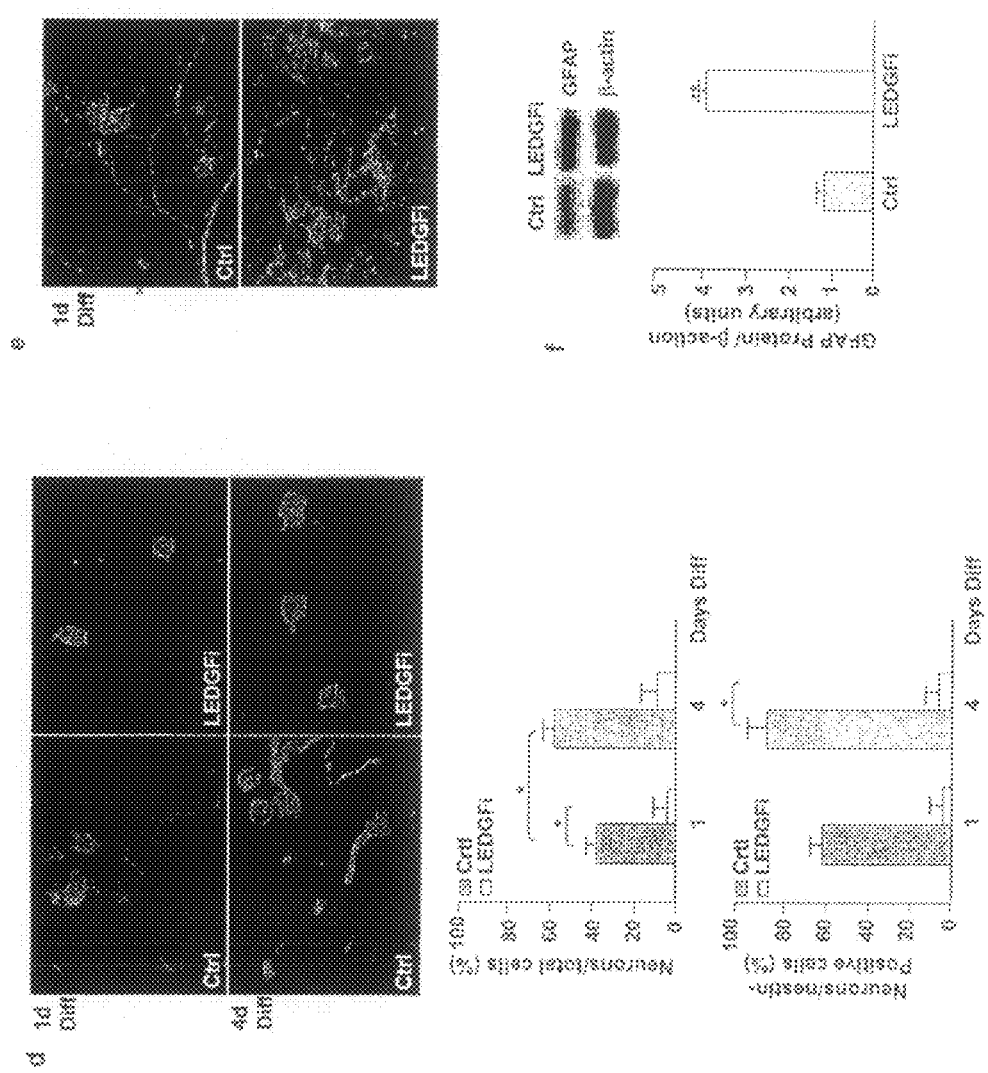

Goldstein

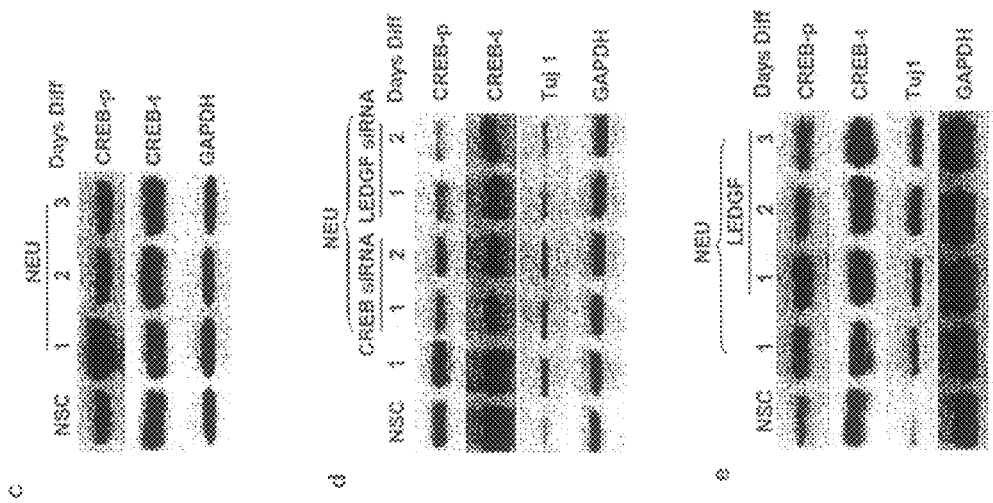

Goldstein

Gottstein

Goldstein

COMPOSITIONS AND METHODS FOR DIAGNOSING TUMORS USING LEDGF/P75

RELATED APPLICATIONS

This application claims priority to U.S. Ser. No. 60/901,740, filed Feb. 16, 2007, which is herein incorporated by reference in its entirety.

FIELD OF THE INVENTION

The instant invention relates generally to the fields of stem cell biology and cancer biology.

BACKGROUND

Neuroepithelial stem cells (NESCs) are stem cells that retain the potential to differentiate into neurons or astrocytes. Although progress has been made in elucidating the regulatory pathways involved in neurogliogenesis, the molecular mechanisms that mediate these functions remain incompletely defined.

Lens epithelium-derived growth factor (LEDGF/p75) (see Singh et al., Invest Ophthalmol Vis Sci 40:1444-51 (1999); and Ge et al., Embo J. 17:6723-29 (1998)) is a transcriptional co-activator that belongs to the hepatoma-derived growth factor (HDGF) superfamily, whose member proteins include auto/paracrine growth factors and survival factors that possess bipartite nuclear localization signals. (See Singh et al., Biochem Biophys Res Commun 267:373-81 (2000)). For example, the HDGF superfamily includes HDGF and HDGF-related proteins. (See Dietz et al., Biochem J 366:491-500 (2002)).

LEDGF/p75 is highly expressed in the lens epithelium (see Singh et al., Biochem Biophys Res Commun 267:373-81 (2000)), which functions as a progenitor cell reservoir on the anterior surface of the crystalline lens. Lens epithelial cells transdifferentiate throughout life to generate long-lived postmitotic lens fiber cells. A marked decrease in lens epithelial cell LEDGF/p75 expression has been shown to be tightly correlated with initiation of lens epithelial cell to fiber cell terminal differentiation. (See Kubo et al., Histochem Cell Biol 119:289-99 (2003)).

SUMMARY OF THE INVENTION

The instant invention provides methods for diagnosing a tumor in a mammal, e.g., a human, by contacting at least one bodily fluid or bodily tissue sample from the mammal with a reagent that binds to LEDGF/p75 or a nucleic acid encoding LEDGF/p75 complementary to the LEDGF/p75 coding sequence under conditions sufficient to form a LEDGF/p75 or nucleic acid reagent complex and detecting said complex. The presence of a complex indicates that the mammal has a tumor. For example, the bodily fluid may be serum or cerebrospinal fluid (CSF). In any of the methods described herein, the LEDGF/p75 nucleic acid may be an mRNA or a DNA molecule. The sequence is a coding sequence or a complement thereof. Subjects from which tissue samples or bodily fluid samples are derived include children as well as adult patients. In various embodiments, the tumor is located in the CNS, the prostate, the skin (e.g., the basal layer of the skin), the bone marrow, or the gut (e.g., the gastrointestinal tract) of the mammal. LEDGF/p75 is used to detect epitheloid cancers and melanomas. By way of non-limiting example, the tumor may be a brain tumor such medulloblastoma, meningioma, astrocytoma, glioblastoma multiforme, and ependymoma.

Also provided are methods for diagnosis of a brain tumor in a patient by identifying cells in the patient that express LEDGF/p75 or a nucleic acid encoding LEDGF/p75; determining the localization of LEDGF/p75 or nucleic acid expression in the identified cells; and comparing this localization information with the LEDGF/p75 or nucleic acid expression pattern from a particular brain tumor in order to diagnose the brain tumor in the patient. For example, the brain tumor may be medulloblastoma, meningioma, astrocytoma, glioblastoma multiforme, and/or ependymoma. When LEDGF/p75 or nucleic acid expression is localized in the nucleus of the cells, those skilled in the art will recognize that this indicates that the patient is suffering from a medulloblastoma. Similarly, when LEDGF/p75 or nucleic acid expression is localized in the cytoplasm of the cells, those skilled in the art will recognize that this indicates that the patient is suffering from a meningioma. Moreover, when LEDGF/p75 or nucleic acid expression is localized in both the nucleus and the cytoplasm of the cells, those skilled in the art will recognize that this indicates that the patient is suffering from a glioma.

The invention also includes methods for the diagnosis of a cancer involving cancerous epithelial cells in a patient by identifying epithelial cells in said patient that express LEDGF/p75 or a nucleic acid encoding LEDGF/p75; determining the localization of LEDGF/p75 or nucleic acid expression in the identified cells; and comparing the localization information with the LEDGF/p75 or nucleic expression pattern from a particular cancer involving cancerous epithelial cells in order to diagnose the cancer in the patient. By way of nonlimiting example, the cancer involving cancerous epithelial cells may be colon cancer or cancer of other gut tissue. LEDGF/p75 is also useful to detect and diagnose other cancer types such as tumors of the breast (e.g., carcinomas), colon (e.g., adenocarcinoma), lung (e.g., squamous cell carcinoma, large cell carcinoma, and adenocarcinoma), lymph tissue (e.g., Non-Hodgkin's lymphoma, B cell, lymph metastatic AC), kidney (e.g., clear cell carcinoma), thyroid (e.g., follicular carcinoma, thyroid adenoma), skin (e.g., melanoma) and prostate.

Methods for determining the prognosis of a brain tumor are also described. For example, the invention provides prognostic methods involving the steps of contacting central nervous system (CNS) tissue of a mammal suffering therefrom with a compound that preferentially binds to LEDGF/p75 or a nucleic acid encoding LEDGF/p75; quantifying the level of association between the compound and LEDGF/p75 or the nucleic acid; and comparing the quantified level of association with a normal control level of association, wherein increasing levels of association over time indicates an adverse prognosis for the patient.

The methods described herein can also be used to isolate stem cells from a heterogeneous population of cells by contacting the population with a reagent that recognizes LEDGF/p75 or a nucleic acid encoding LEDGF/p75 under conditions that allow the reagent to form a complex with cells expressing LEDGF/p75 or the nucleic acid. For example, the stem cell can be an epitheliod stem cell such as a neuroepithelial stem cell. Suitable reagents, include, but are not limited to, antibodies. In some embodiments, the antibody is detectably labeled with a label. Examples of suitable detectable labels include, but are not limited to magnetic beads, magnetic reagents, superparamagnetic microparticles, biotin, fluorochromes, and haptens. These isolation methods can also involve the additional step of removing the complex to yield a population enriched for stem cells.

Also provided herein are methods for identifying specific cell types in a subject by administering a reagent that recognizes LEDGF/p75 or a nucleic acid encoding LEDGF/p75 to the subject; allowing the reagent to form a complex with those cells expressing LEDGF/p75 or the nucleic acid; detecting the presence of complexes within the subject, if any, and determining the location of the complex within the cell. The presence of identified complexes within the cytoplasm identifies the cell as a neuroepithelial stem cell. Similarly, the presence of complexes within the nucleus identifies the cell as a newly differentiated neuron, while the absence of complexes identifies the cell as an astrocyte. The methods described herein can also be used to identify tumor cells.

Knockdown of LEDGF/p75 enhances astrocytic differentiation, and LEDGF/p75 affects proliferation of neural stem cells and astrocytes. Enhancing expression of LEDGF/p75 protein or nucleic acid increases neuronal differentiation. Neural stem cells and astrocytes were transfected with either LEDGF/p75 siRNA or vector. Mass (tumor) formation was detected in a brain site after injection with LEDGF/p75 siRNA-treated cells (as detected by MRI). In tissue biopsies from meningioma, medulloblastoma, and glioma tumors, expression of LEDGF/p75 was found to be high in the tumors compared to non-tumor tissue. Localization of expression was found to be cell-specific: nuclear expression in medulloblastoma (which arises in cerebellum in children); cytoplasmic expression in meningioma (which arise from arachnoid cap); and both nuclear and cytoplasmic expression in gliomas.

Contacting one or more neuroepithelial stem cells with an agent that downregulates LEDGF/p75 protein and mRNA expression in the neuroepithelial stem cells can induce the NESCs to differentiate into astrocytes. Those skilled in the art will recognize that suitable downregulating agents can include, for example, a lentiviral LEDGF/p75 RNAi vector, a LEDGF/p75 antagonist, and/or an anti-LEDGF/p75 antibody. Other downregulating agents commonly used by those skilled in the art can also be used to induce NESC differentiation into astrocytes. Similarly, contacting one or more neuroepithelial stem cells with an agent that upregulates nuclear LEDGF/p75 protein expression in the neuroepithelial stem cells can be used to induce the NESCs to differentiate into neurons. For example, the upregulating agent may be an LEDGF/p75 agonist. Other upregulating agents commonly used by those skilled in the art can also be used to induce NESC differentiation into neurons.

Modulating the expression of LEDGF/p75 can also be used in the treatment of various cancers. For example, in many cancers, LEDGF/p75 is inappropriately expressed. Examples of such cancers include, for example, neuroepithelial cancers, medulloblastoma, embryonal tumors, CNS primitive neuroectodermal tumors (PNETs), medulloepitheliomas, ependymoblastomas, atypical teratoid rhabdoid tumors, glioblastoma multiforme (GBM) and related astrocytic tumors, and the like. Similar inappropriate LEDGF/p75 expression has also been observed in tumors located in the prostate, gastrointestinal tract, skin (e.g., basal layer of the skin), and bone marrow.

Those skilled in the art will recognize that when LEDGF/p75 is overexpressed in a given tumor or cancer, use of an agent that downregulates LEDGF/p75 protein or nucleic acid expression can be used to treat the tumor or cancer. Examples of such agents may include, for example, a lentiviral LEDGF/p75 RNAi vector, a LEDGF/p75 antagonist, and/or an anti-LEDGF/p75 antibody. Similarly, when LEDGF/p75 is underexpressed in a given tumor or cancer, use of an agent that upregulates LEDGF/p75 protein or nucleic acid expression can be used to treat the tumor or cancer. For example, the upregulating agent may be an LEDGF/p75 agonist.

LEDGF/p75 can also be used in methods to screen for candidate compounds that regulate the differentiation of NESCs. Specifically, a population of cells containing neuroepithelial stem cells that express LEDGF/p75 or a nucleic acid encoding LEDGF/p75 can be exposed to a candidate compound, and the effect, if any, of the candidate compound on LEDGF/p75 or nucleic acid expression or localization or both within said cells can be determined. LEDGF/p75 or nucleic acid expression and/or localization following such exposure is then compared with normal control LEDGF/p75 or nucleic acid expression and/or localization. Those skilled in the art will recognize that a difference in LEDGF/p75 or nucleic acid expression and/or localization following exposure to the candidate compound indicates that the candidate compound regulates or influences the differentiation of neuroepithelial stem cells. Specifically, when LEDGF/p75 or nucleic acid expression and/or localization occurs in the nucleus following exposure to the candidate compound, the candidate compound influences neuroepithelial stem cell differentiation into neurons. Likewise. the absence of LEDGF/p75 or nucleic acid expression and/or localization following exposure to the candidate compound indicates that the candidate compound influences neuroepithelial stem cell differentiation into astrocytes.

Also provided are methods for modulating CREB expression and activation in neuroepithelial stem cells by administering an effective amount of a LEDGF/p75 or an LEDGF/p75 agonist to at least one neuroepithelial stem cell, wherein CREB expression and activation is modulated. For example, CREB expression and activation can be upregulated following the administration of LEDGF/p75 or the LEFGF/p75 agonist. Such upregulation results in neuroepithelial stem cell differentiation into neurons.

As used throughout, the terms "reagent", "compound that preferentially binds" and "compound" are meant to include any composition or compound that is capable of binding to, associating with, or recognizing LEDGF/p75 or a nucleic acid encoding LEDGF/p75. Examples of such reagents include, but are not limited to monoclonal antibodies, polyclonal antibodies, small molecules, receptors, ligands, proteins, protein fragments, polypeptides, polypeptide fragments, nucleic acids, nucleic acid fragments, antibody fragments, and any other "reagents" known to those skilled in the art. The use of traditional techniques for cell sorting, such as by immunoselection (e.g., FACS), then permits identification, isolation, and/or enrichment for cells in which contact between the reagent or compound and LEDGF/p75 or a nucleic acid encoding LEDGF/p75. In various embodiments, the reagent or compound may be fluorochrome conjugated or may be conjugated to magnetic particles such as a superparamagnetic microparticle. Conveniently, the reagents or compounds are conjugated with labels to allow for ease of separation of the particular cell type, e.g magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Fluorochromes which find use in a multi-color analysis include phycobiliproteins, e.g. phycoerythrin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control.

Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the reagent or compound and a reactive amino group on the magnetic particle.

Alternatively, the reagent or compound is indirectly coupled to the magnetic particles. Specifically, the reagent or compound is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

Selecting may be by fluorescence activated cell sorting, high gradient magnetic selection, by attachment to and disattachment from the solid phase, or by any other technique routinely used by those of ordinary skill in the art. Likewise, procedures for separation or selection may include magnetic separation, using antibody-coated magnetic beads, affinity chromatography and "panning" with antibody attached to a solid matrix, e.g. plate, or other convenient technique routinely used by those of ordinary skill in the art. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (e.g., propidium iodide [PI], LDS). Any other techniques commonly used in the art may be employed which is not unduly detrimental to the viability of the selected cells.

To practice these methods, the reagent or compound is added to a cell sample. The amount of reagent or compound necessary to bind a particular cell subset is empirically determined by performing a test separation and analysis. The cells and reagent or compound are incubated for a period of time sufficient for complexes to form, usually at least about 5 min, more usually at least about 10 min, and usually not more than one hour, more usually not more than about 30 min.

The cells may additionally be incubated with antibodies or binding molecules specific for cell surface markers known to be present or absent on the cells.

The labeled cells are separated in accordance with the specific reagent or compound preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520.

The purified cell populations and/or complexes may be collected in any appropriate medium. Various media are commercially available and may be used, including Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc. By "specifically binds" is meant an antibody that recognizes and binds an antigen or antigenic domain of LEDGF/p75 but that does not substantially recognize and bind other non-antigen molecules in a sample, e.g., a biological sample, that naturally includes protein or domains of a target protein.

By "high stringency conditions" is meant any set of conditions that are characterized by high temperature and low ionic strength and allow hybridization comparable with those resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. See, e.g., F. Ausubel et al., Current Protocols in Molecular Biology, John Wiley & Sons, New York, N.Y., 1998, hereby incorporated by reference.

By "substantially pure" is meant a nucleic acid, polypeptide, or other molecule that has been separated from the components that naturally accompany it. Typically, the polypeptide is substantially pure when it is at least 60%, 70%, 80%, 90%, 95%, or even 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "candidate compound" is meant a chemical, be it naturally-occurring or artificially-derived. Candidate compounds may include, for example, peptides, polypeptides, synthetic organic molecules, naturally occurring organic molecules, nucleic acid molecules, peptide nucleic acid molecules, and components and derivatives thereof. The term "pharmaceutical composition" is meant any composition, which contains at least one therapeutically or biologically active agent and is suitable for administration to the patient. Any of these formulations can be prepared by well-known and accepted methods of the art. See, for example, Remington: The Science and Practice of Pharmacy, 20th edition, (ed. A. R. Gennaro), Mack Publishing Co., Easton, Pa., 2000.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source and are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO: 1, 3, 5, 7, 8, 9, 10, 11, or 12 or a complement thereof. Oligonucleotides may be chemically synthesized and may be used as probes.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Van der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Probes based on the LEDGF/p75 nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which express or misexpress LEDGF/p75 protein, such as by measuring a level of a LEDGF/p75-encoding nucleic acid in a sample of cells from a subject e.g., detecting LEDGF/p75 mRNA levels or determining whether a genomic LEDGF/p75 gene has been mutated or deleted.

The invention also provides a diagnostic reagent pack or kit containing one or more containers filled with one or more of the agents of the invention. Reagents for carrying out the diagnostic or prognostic assay may be packaged together as a kit. For example, the antibody is immobilized on a solid phase and packaged together with other reagents suitable for detecting the peptide-antibody complexes. The pack or kit can be labeled with information regarding the sequence of execution, or the like. The pack or kit can be a single unit assay or it can be a plurality of unit assays. For the purpose of this invention, unit assays is intended to mean materials sufficient to perform only a single assay.

Those skilled in the art will recognize that the detection methods of the invention can be used to detect LEDGF/p75 mRNA, polypeptide, or genomic DNA in a biological sample in vitro as well as in vivo. For example, in vitro techniques for detection of LEDGF/p75 mRNA include Northern hybridizations and in situ hybridizations. In vitro techniques for detection of LEDGF/p75 polypeptide include enzyme linked immunosorbent assays (ELISAs), Western blots, immunoprecipitations and immunofluorescence. In vitro techniques for detection of LEDGF/p75 genomic DNA include Southern hybridizations. Furthermore, in vivo techniques for detection of LEDGF/p75 protein include introducing into a subject a labeled anti-LEDGF/p75 antibody. For example, the antibody can be labeled with a radioactive marker whose presence and location in a subject can be detected by standard imaging techniques.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

BRIEF DESCRIPTION OF THE DRAWINGS

FIGS. 1A-1C show representative doublestaining in fetal cortical mantle, while FIGS. 1D-1F show representative doublestaining in adult SVZ.

FIG. 3A is a series of photomicrographs demonstrating the efficiency of LEDGF/p75 knockdown NESCs as determined by IFC. FIG. 3B is a Western blot showing the efficiency of LEDGF/p75 knockdown in NESCs. FIGS. 3A and 3B show decreased neuron production and increased astrocytes production in LEDGF/p75 knockdown NESCs in culture. FIG. 3C is a series of photomicrographs demonstrating the quantification of LEDGF/p75 protein knockdown by shRNA lentivirus and showing that the knockdown of LEDGF/p75 reduces neuron production. FIG. 3D is a series of photomicrographs demonstrating that neuron production was examined by immunostaining for Tuj1 after one or four days differentiating. The number of neurons produced is shown as a percentage of the total number of cells (upper) or as a percentage of nestin$^+$ cells (lower). FIG. 3E is a series of photomicrographs demonstrating that astrocyte differentiation is promoted in knockdown NESCs as shown by IFC. FIG. 3F is a Western blot analysis (upper) and quantification of GFAP protein expression (lower). Asterisks indicate increased expression of GFAP in LEDGF/p75i treated cells.

FIGS. 4A-D show that the expression and activation of CREB were regulated by LEDGF/p75 and that CREB Ser133 phosphorylation is required for neuronal differentiation.

DETAILED DESCRIPTION

Figure 1:
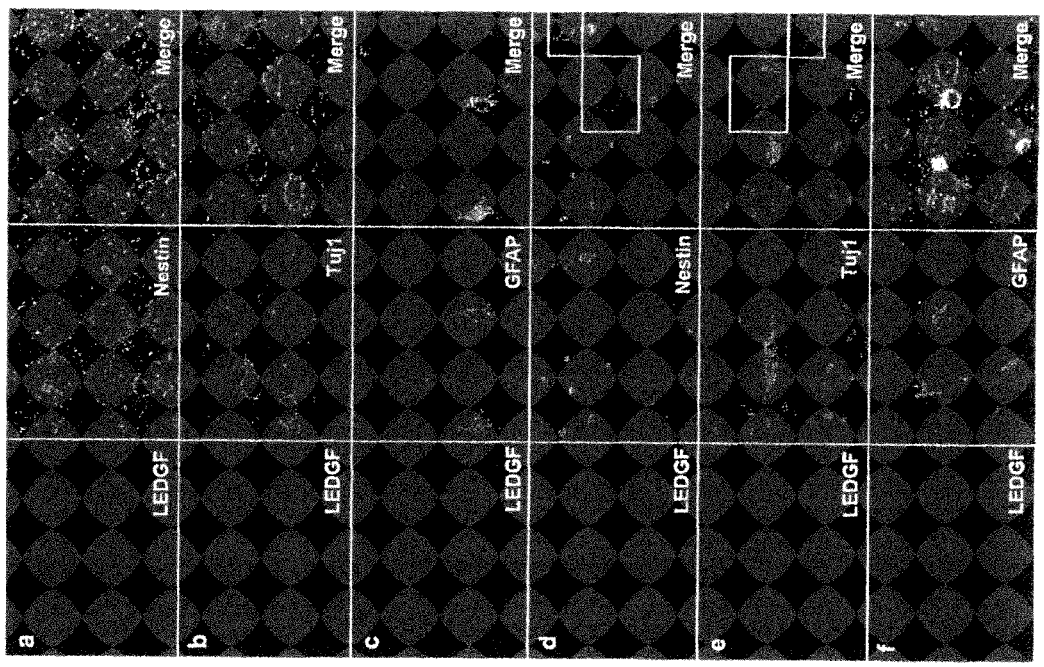
FIGS. 1A-F are a series of photomicrographs demonstrating that LEDGF/p75 localizes to the cytoplasm in nestin$^+$ NESCs, the nucleus in Tuj-1$^+$ immature neurons, and is absent from GFAP$^+$ astrocytes in fetal and adult human SVZ.

Development of the mammalian central nervous system is dependent on regulated differentiation of neuroepithelial stem cells (NESCs) along distinct neuronal and glial pathways. Aberrant NESC differentiation has been implicated in brain tumorogenesis.

LEDGF/p75 (GenBank GeneID: 11168) is a transcription activator protein that is highly expressed in the germinal neuroepithelium and cortical mantle of the developing fetal human brain and in the subventricular zone (SVZ) of the adult human brain. (See Chylak et al., Exp Eye Res 79:941-48 (2004)). These brain regions are enriched in neuroepithelial progenitor cells, which give rise to the neurons and glia that populate the adult brain. Based on this data, as well as the ectodermal embryological origin of both the lens and brain and the epithelial nature of the progenitor cell reservoir in both organs, LEDGF/p75 and its allied signaling pathways might regulate NESC fate determination and early neuroglial differentiation in the brain. Moreover, because LEDGF/p75 is involved in acute and chronic myeloid leukemias (see Hussey et al., BMC Genet 2:20 (2001)) and is highly expressed in prostate cancer (see Daniels et al., Prostate 62:14-26 (2005)), aberrant regulation of this transcription factor might be associated with CNS tumorigenesis.

Nucleic acid and protein sequences for LEDGF/p75 are provided below.

```
GenBank Accession No. AF098482 (SEQ ID NO: 24):
    1 gaattcgcgg ccgccccgcg ccgccgcatc tcctcgccgc ctcccgggct tcggacccc
   61 ggtctcgccc ccgaaacatg actcgcgatt tcaaacctgg agacctcatc ttcgccaaga
  121 tgaaaggtta tccccattgg ccagctcgag tagacgaagt tcctgatgga gctgtaaagc
  181 cacccacaaa caaactaccc attttctttt ttggaactca tgagactgct tttttaggac
  241 caaaggatat atttccttac tcagaaaata aggaaaagta tggcaaacca aataaaagaa
  301 aaggttttaa tgaaggttta tgggagatag ataacaatcc aaaagtgaaa ttttcaagtc
  361 aacaggcagc aactaaacaa tcaaatgcat catctgatgt tgaagttgaa gaaaaggaaa
  421 ctagtgtttc aaaggaagat accgaccatg aagaaaaagc cagcaatgag gatgtgacta
  481 aagcagttga cataactact ccaaaagctg ccagaagggg gagaaagaga aaggcagaaa
  541 aacaagtaga aactgaggag gcaggagtag tgacaacagc aacagcatct gttaatctaa
  601 aagtgagtcc taaaagagga cgacctgcag ctacagaagt caagattcca aaaccaagag
  661 gcagacccaa aatggtaaaa cagccctgtc cttcagagag tgacatcatt actgaagagg
  721 acaaaagtaa gaaaaagggg caagagggaa acaacctaa aaagcagcct aagaaggatg
  781 aagagggcca gaaggaagaa gataagccaa gaaaagagcc ggataaaaaa gagggaaga
  841 aagaagttga atcaaaaagg aaaaatttag ctaaaacagg ggttacttca acctccgatt
  901 ctgaagaaga aggagatgat caagaaggtg aaaagaagag aaaaggtggg aggaactttc
  961 agactgctca cagaaggaat atgctgaaag gccaacatga gaaagaagca gcagatcgaa
 1021 aacgcaagca agaggaacaa atggaaactg agcaccaaac aacatgtaat ctacagtaat
 1081 aaaaaatata tctcattttg ggctcaaagc attaatccag ttactgaaaa gagaatacaa
 1141 gtggagcaaa caagagatga agatcttgat acagactcat tggactgaat ttccccttc
 1201 ccccatgat ggaagaatgt tcagattcta aattgaggac ttcattatta atggcattac
 1261 tgtgttatga ttaacaaatt tcttgtaagg tacacactac atactaaggt cggccatcat
```

```
                                                     -continued
1321  tccgttttt  ttttttttt  tttttttaac  caagcttaaa  atgaagctta  aaatgaagct 1381  ttgtgtttga  aagtaataac  aagctcagac  gaagatggtg  gttgtacatt  attcatctag 1441  aaaatataaa  aattcatttt  gttttgaagc  tagttattaa  actggaatag  cagttatatc 1501  cctgagaatg  gggcccttct  cttgacattc  cttttgttgt  ttaattcttt  agaatcttaa 1561  taaatgtttt  tttaatcctg  agagattaaa  cagtagtaga  cttgttaaga  atgaaactgt 1621  aaccaaaatt  ttaaaataaa  gttttttta  aaaaaaaaaa  aaaaaaaaaa  aaaaaaa GenBank Accession No. AAC25167 (SEQ ID NO: 25):
    1  mtrdfkpgdl  ifakmkgyph  wparvdevpd  gavkpptnkl  pifffgthet  aflgpkdifp 61  ysenkekygk  pnkrkgfneg  lweidnnpkv  kfssqqaatk  qsnassdvev  eeketsvske 121  dtdheekasn  edvtkavdit  tpkaarrgrk  rkaekqvete  eagvvttata  svnlkvspkr 181  grpaatevki  pkprgrpkmv  kqpcpsesdi  iteedkskkk  gqeekqpkkq  pkkdeegqke 241  edkprkepdk  kegkkevesk  rknlaktgvt  stsdseeegd  dqegekkrkg  grnfqtahrr 301  nmlkgqheke  aadrkrkqee  qmeteqqnkd  egkkpevkkv  ekkretsmds  rlqrihaeik 361  nslkidnldv  nrciealdel  aslqvtmqqa  qkhtemittl  kkirrfkvsq  vimekstmly 421  nkfknmflvg  egdsvitqvl  nkslaeqrqh  eeanktkdqg  kkgpnkklek  eqtgsktlng 481  gsdaqdgnqp  qhngesneds  kdnheastkk  kpsseerete  islkdstldn GenBank Accession No. AAF25871 (SEQ ID NO: 26):
    1  mtrdfkpgdl  ifakmkgyph  wparvdevpd  gavkpptnkl  pifffgthet  aflgpkdifp 61  ysenkekygk  pnkrkgfneg  lweidnnpkv  kfssqqaatk  qsnassdvev  eeketsvske 121  dtdheekasn  edvtkavdit  tpkaarrgrk  rkaekqvete  eagvvttata  svnlkvspkr 181  grpaatevki  pkprgrpkmv  kqpcpsesdi  iteedkskkk  gqeekqpkkq  pkkdeegqke 241  edkprkepdk  kegkkevesk  rknlaktgvt  stsdseeegd  dqegekkrkg  grnfqtahrr 301  nmlkgqheke  aadrkrkqee  qmetehqttc  nlq GenBank Accession No. AAF25870 (SEQ ID NO: 27):
    1  mtrdfkpgdl  ifakmkgyph  wparvdevpd  gavkpptnkl  pifffgthet  aflgpkdifp 61  ysenkekygk  pnkrkgfneg  lweidnnpkv  kfssqqaatk  qsnassdvev  eeketsvske 121  dtdheekasn  edvtkavdit  tpkaarrgrk  rkaekqvete  eagvvttata  svnlkvspkr 181  grpaatevki  pkprgrpkmv  kqpcpsesdi  iteedkskkk  gqeekqpkkq  pkkdeegqke 241  edkprkepdk  kegkkevesk  rknlaktgvt  stsdseeegd  dqegekkrkg  grnfqtahrr 301  nmlkgqheke  aadrkrkqee  qmeteqqnkd  egkkpevkkv  ekkretsmds  rlqrihaeik 361  nslkidnldv  nrciealdel  aslqvtmqqa  qkhtemittl  kkirrfkvsq  vimekstmly 421  nkfknmflvg  egdsvitqvl  nkslaeqrqh  eeanktkdqg  kkgpnkklek  eqtgsktlng 481  gsdaqdgnqp  qhngesneds  kdnheastkk  kpsseerete  islkdstldn
```

Methods for Identification, Localization, Diagnosis, Prognosis, and Staging of Tumors LEDGF/p75 is differentially expressed and discretely localized in diverse brain tumors and other tumor types (see Tables 1-4). Expression and subcellular localization patterns differ among tumor types. LEDGF/p75 is useful as a tumor biomarker for screening tissues or fluids for diagnostic purposes as well as evaluation of response to treatment. The marker is also useful for purification/isolation of tumor cells. As a secreted protein, LEDGF/p75 measurements obtained from serum and/or CSF is useful as a peripheral biomarker of tumor screening, presence, burden, and treatment response.

TABLE 1

LEDGF/p75 protein IHC staining in brain tumor TMA

| Loc | Brain Array | ID | Nuc score | Cyt score | BKS |
|---|---|---|---|---|---|
| 1 | Brain 1 | Ependymoma | | 2 | +/− |
| 2 | Brain 5 | Astrocytoma | 2 | | +/− |
| 3 | Brain 7 | Mixed astrocytoma | 1 | | +/− + |
| 4 | Brain 9 | Astrocytoma | | | +/− |
| 5 | Brain 10 | Astrocytoma | 0 | | + |
| 6 | Brain 11 | Astrocytoma | No tissue | | |
| 7 | Brain 12 | Oligodendroglioma | 1 | | +/− + |
| 8 | Brain 13 | Astrocytoma | No tissue | | |
| 9 | Brain 14 | Astrocytoma | No tissue | | |
| 10 | Brain 15 | Astrocytoma | No tissue | | |
| 11 | Brain 16 | Oligodendroglioma | | 1 | +/− + |
| 12 | Brain 17 | Astrocytoma | 2 | | +/− + |
| 13 | Brain 18 | Astrocytoma | No tissue | | |
| 14 | Brain 19 | Mixed astrocytoma | | | − |
| 15 | Brain 20 | Ependymoma | 3 | | + |
| 16 | Brain 3 | Meningioma | 1 | 3 | +/− + |
| 17 | Brain 4 | Meningioma | | 3 | − |
| 18 | Brain 21 | Malignant meningioma | | | − |
| 19 | Brain 24 | Benign meningioma | | 2 | +/− |
| 20 | Brain 25 | Benign meningioma | | 1 | +/− |
| 21 | Brain 26 | Benign meningioma | | | + |
| 22 | Brain 27 | Benign meningioma | | 2 | +/− |
| 23 | Brain 28 | Benign meningioma | | 2 | +/− |
| 24 | Brain 29 | Atypical meningioma | | 1 | +/− |
| 25 | Brain 30 | Benign meningioma | | 2 | − |
| 26 | Brain 31 | Atypical meningioma | | 1 | +/− |
| 27 | Brain 32 | Benign meningioma | | 3 | − +/− |
| 28 | Brain 2 | Medulloblastoma | 3 | | +/− |
| 29 | Brain 22 | Medulloblastoma | 3 | | +/− |
| 30 | Neuro 3 | Medulloblastoma | 3 | | − +/− |
| 31 | Neuro 4 | Medulloblastoma | 3 | | +/− |
| 32 | Neuro 5 | Medulloblastoma | 3 | | − +/− |
| 33 | Neuro 6 | Medulloblastoma | 1 | | − +/− |
| 34 | Neuro 7 | Medulloblastoma | 3 | | − +/− |
| 35 | Neuro 8 | Medulloblastoma | 3 | | +/− |
| 36 | Neuro 9 | Medulloblastoma | 2 | | − +/− |
| 37 | Neuro 10 | Medulloblastoma | 3 | | +/− |
| 38 | Neuro 11 | Medulloblastoma | 2 | | +/− + |

TABLE 2

LEDGF/p75 antibody IHC staining in colon tissues

| CST Name | ID | Nuc score | Cyt score | Note |
|---|---|---|---|---|
| Lg intestine 1, grade 1-2 | AC (adenocarcinoma) | 0 | 0 | |
| Lg intestine 2, grade 1-2 | AC | 0 | 1 | |
| Lg intestine 3, grade 2 | AC | 0 | 1 | |
| Lg intestine 4, grade 1-2 | AC | 0 | 0 | |
| Lg intestine 5, grade 1-2 | AC | 0 | 0 | Plasacyte (++) |
| Lg intestine 6, grade 1 | AC | 0 | 0 | Plasacyte (++) |
| Colon 8, grade 1 | AC | 0 | 0 | |
| Colon 9, grade 1-2 | AC | 0 | 0 | Granular staining in cancer cells, artifact? |
| Colon 10, grade 1-2 | AC | 0 | 0 | |
| Colon 11, grade 1 | AC | 0 | 0 | |
| Colon 12, grade 1-2 | AC | 0 | 0 | Granular staining in cancer cells, artifact? |
| Colon 13, grade 2 | AC | 0 | 0 | |
| Colon 14, grade 1 | AC | 0 | 2 | |
| Colon 15, grade 1 | AC | 0 | 0 | Granular staining in cancer cells, artifact? |
| Colon 16, grade 2 | AC | 0 | 0 | Granular staining in cancer cells, artifact? |
| Colon 18, grade 3 | AC | 0 | 1 | Plasacyte (++) |
| Colon 19, grade 2 | AC | 0 | 0 | Granular staining in cancer cells, artifact? |
| Colon 20, grade 1 | AC | 0 | 0 | |
| Colon 22, grade 1-2 | AC | 0 | 0 | Granular staining in cancer cells, artifact? |
| Colon 23, grade 2 | AC | 0 | 0 | Granular staining in cancer cells, artifact? |
| Colon 24, grade 3 | AC | 0 | 0 | |
| Colon 25, grade 2 | AC | 0 | 0 | Granular staining in cancer cells, artifact? |

TABLE 2-continued

LEDGF/p75 antibody IHC staining in colon tissues

| CST Name | ID | Nuc score | Cyt score | Note |
|---|---|---|---|---|
| Colon 26, grade 2 | AC | No tissue | | |
| Colon 27, grade 2 | AC | 0 | 1 | |
| Colon 28, grade 1-2 | AC | 0 | 0 | Granular staining in cancer cells, artifact? |
| Colon 29, grade 1 | AC | 0 | 2 | With some granular staining in cancer cells, artifact? |
| Colon 30, grade 2-3 | AC | 0 | 2 | With some granular staining in cancer cells, artifact? |
| Colon 31, grade 1 | AC | 0 | 0 | Granular staining in cancer cells, artifact? |
| Colon 32, grade 2 | AC | 0 | 0 | |
| Colon 33, grade 3 | AC | 0 | 0 | |
| Colon 34, grade 3 | AC | 0 | 0 | |
| Colon 35, grade 3 | AC | 0 | 0 | |
| Colon 36, grade 1-2 | AC | 0 | 1 2 | |
| Colon 37, grade 1 | AC | 0 | 1 | With some granular staining in cancer cells, artifact? |
| Colon 38, grade 1-2 | AC | 0 | 0 | |
| Colon 39, grade 2 | AC | 0 | 0 | |
| Colon 40, grade 1 | AC | 0 | 0 | Granular staining in cancer cells, artifact? |
| Colon 41, grade 1 | AC | 0 | 0 | Granular staining in cancer cells, artifact? |
| Colon 43, grade 2 | AC | 0 | 2 | |
| Colon 44, grade 3 | AC | No tissue | | |
| Colon 46, grade 1 | AC | 0 | 0 | |
| Colon 47, grade 1 | AC | 0 | 0 | Granular staining in cancer cells, artifact? |
| Colon 48, grade 2 | AC | 0 | 0 | |
| Colon 49, grade 2 | AC | 0 | 0 | |
| Colon 50, grade 2 | AC | 0 | 0 | Granular staining in cancer cells, artifact? |
| Colon 51, grade 3 | AC | 0 | 0 | |
| Colon 52, grade 3 | AC | 0 | 1 | |
| Colon 53, grade 2 | AC | 0 | 0 1 | |
| Colon 54, grade 1 | AC | 0 | 0 | Granular staining in cancer cells, artifact? |
| Colon 55, grade 3 | AC | Undecided | 0 | |
| Colon 56, grade 1 | AC | 0 | 1 | |
| Colon 57, grade 1-2 | AC | 0 | 0 | Granular staining in cancer cells, artifact? |
| Colon 58, grade 2-3 | AC | 0 | 0 | Granular staining in cancer cells, artifact? |
| Normal 16 | Normal mucosa | 0 | 0 | Granular staining in normal epithelial cells, artifact? Plasacyte (++) |
| Normal 17 | Normal mucosa | 0 | 0 | Granular staining in normal epithelial cells, artifact? |
| Normal 18 | Normal mucosa | No tissue | | |
| Normal 19 | Normal mucosa | 0 | 0 | Plasacyte (++) |
| Normal 20 | Normal mucosa | No tissue | | |
| Lg intestine 2 | Normal mucosa + AC | 0 | 0 | Granular staining in normal epithelial cells, artifact? Plasacyte (++) |
| Lg intestine 4 | AC | 0 | 0 | |
| Lg intestine 6 | Normal mucosa | No tissue | 0 | |
| Colon 11 | Normal mucosa | No tissue | 0 | |
| Colon 12 | Normal mucosa | 0 | 0 | Granular staining in normal epithelial cells, artifact? Plasacyte (++) |
| Colon 17 | Normal mucosa | 0 | 0 | Granular staining in normal epithelial cells, artifact? Plasacyte (++) |
| Colon 23 | Normal mucosa | 0 | 0 | Granular staining in normal epithelial cells, artifact? Plasacyte (++) |

TABLE 2-continued

LEDGF/p75 antibody IHC staining in colon tissues

| CST Name | ID | Nuc score | Cyt score | Note |
|---|---|---|---|---|
| Colon 26 | Normal mucosa | 0 | 0 | |
| Colon 28 | Normal mucosa | 0 | 0 | Granular staining in normal epithelial cells, artifact? |
| Colon 29 | Normal mucosa | 0 | 0 | Granular staining in normal epithelial cells, artifact? |
| Colon 32 | AC | 0 | 1 | With some granular staining in cancer cells, artifact? |
| Colon 46 | Normal mucosa | No tissue | | |
| Colon 49 | AC | 0 | 1 | |
| Colon 50 | Normal mucosa | No tissue | | |
| Colon 52 | Normal mucosa | 0 | 0 | Granular staining in cancer cells, artifact? Plasacyte (++) |
| Colon 54 | Normal mucosa | 0 | 0 | Granular staining in cancer cells, artifact? Plasacyte (++) |

As shown in Table 2, protein can only be detected in cytoplasm of some cancer cells and is not detected in nuclei or normal or cancerous epithelial cells. These results are different from those observed with brain tumors. The positive frequency is about 26% (13/50) in colon cancer. No positive staining is found in normal colon mucosa (0/17). Granular staining can be seen in normal and cancerous epithelial cells, which may be associated with secreta of colon epithelial cells (normal and cancerous). As secreta sometimes nonspecifically adhere to some antibodies, this observed staining may be an artifact. Some plasacytes in stroma show cytoplasma staining, which may be non-specific binding.

TABLE 3

C-multi-tumor array 11.1(2)

| 1 | 2 | 3 | 4 | 5 |
|---|---|---|---|---|
| 6 | 7 | 8 | 9 | 10 |
| 11 | 12 | 13 | 14 | 15 |
| 16 | 17 | 18 | 19 | |

TABLE 4

| Location | CST NAME | ID | LEDGF/p75 |
|---|---|---|---|
| 1 | Breast 42 | Infiltrative lobular carcinoma | Scattered nuclear and cytoplasmic |
| 2 | Breast 43 | Carcinoma simolex | Negative |
| 3 | Breast 44 | Infiltrative ductal carcinoma | Scattered cyto and endothelial |
| 4 | Breast 45 | Infiltrative lobular carcinoma | Light cyto |
| 5 | Colon 59 | Adenocarcinoma | Light cyto |
| 6 | Colon 60 | Adenocarcinoma | Scattered med to strong cyto |
| 7 | Colon 61 | Adenocarcinoma | Weak cyto and some membrane |
| 8 | Colon 62 | Adenocarcinoma | Particulate; base column cells |
| 9 | Lung 100 | Squamous cell carcinoma | Strong nuclear |
| 10 | Lung 102 | Large cell carcinoma | Med cyto |
| 11 | Lung 103 | Adenocarcinoma | Med cyto |
| 12 | Lung 105 | Adenocarcinoma | Weak nuclear & some cyto |
| 13 | Lymphoma 13 | Non-Hodgkin's lymphoma B cell | Strong nuclear |
| 14 | Lymphoma 43 | Lymphoma | Scattered med cyto |
| 15 | Kidney 1 | Clear cell carcinoma | Slight nuclear |
| 16 | Kidney 4 | Clear cell carcinoma | Weak cyto |
| 17 | Thyroid 4 | Follicular carcinoma | Med cyto |
| 18 | Thyroid 5 | Thyroid adenoma | Med cyto |
| 19 | Other 6 | Lymph metastic AC | Weak cyto |

Translocation of LEDGF/p75 to the NESC nucleus is likely to be a critical step during NESC terminal differentiation. LEDGF/p75 has been implicated in regulating stress-related anti-apoptotic proteins including Hsp27, αB-crystallin (see Singh et al., Invest Ophthalmol Vis Sci 40:1444-51 (1999), Singh et al., Biochem Biophys Res Commun 267: 373-81 (2000); and Singh et al., Biochem Biophys Res Commun 283:943-55 (2001)), and AOP2 (see Fatma et al. J Biol Chem 276:48899-907 (2001)). Upregulation of these proteins is initiated by LEDGF/p75 binding to the heat shock elements (HSEs) and stress-related regulatory elements (STREs) located within the promoter region of these stress-related genes. (See Singh et al., Biochem Biophys Res Commun 283:943-55 (2001)). Thus, LEDGF/p75 may mediate multiple cellular functions, including those involved in neurogliogenesis, by differential protein-DNA binding and transcriptional regulation of key target genes.

The cyclic-AMP response element binding protein (CREB) is another multifunctional nuclear transcription factor that is involved in neuronal development. (See Nakagawa et al., J Neurosci 22:3673-82 (2002); and Fujioka et al., J Neurosci 24:319-28 (2004)). CREB is a basic/leucine zipper transcription factor that binds the cyclic AMP response element (CRE) and activates transcription in response to a variety of extracellular signals including neurotransmitters, hormones, membrane depolarization, and growth neurotrophic factors. Activation of CREB is dependent upon the phosphorylation of serine 133, which occurs via p44/42 MAP kinase and p90RSK and also via p38 MAP kinase and MSKI. Although CREB will bind DNA independently of its phosphorylation state, only the phosphorylated form is competent as a transcription factor. Thus, CREB that is phosphorylated on Serine 133 might promote the binding of CREB to a CREB-binding protein (CBP). CBP, upon binding CREB, then interacts directly with the RNA polymerase II complex, which mediates the initiation of transcription.

CREB expression and phosphorylation are sufficient to induce granule cell differentiation during cerebellum development (see Pons et al., Development 128:1481-92 (2001)), and also to regulate differentiation of newborn neurons in the olfactory bulb and SVZ. (See Fujioka et al., J Neurosci 24:319-28 (2004); and Giachino et al., J. Neurosci 25:10105-18 (2005)). Conversely, dominant-negative CREB mutants exhibit reduced neuronal proliferation and differentiation within the hippocampus. (See Nakagawa et al., J Neurosci 22:3673-82 (2002); and Fujioka et al., J Neurosci 24:319-28 (2004)). Thus, these results implicate CREB as an important player in neuronal proliferation and differentiation.

LEDGF/p75 regulation of neuronal differentiation is mediated through expression and activation of CREB. The mRNA and protein expression patterns of LEDGF/p75 and CREB are parallel and are coordinated with neuronal differentiation. Recent data establishes that LEDGF/p75 is a key regulator of NESCs differentiation and neuroglial cell fate determination. Moreover, aberrant expression of LEDGF/p75 may trigger pro-oncogenic signaling during CNS tumorigenesis.

LEDGF/p75 is a transcription co-activator that is capable of activating multiple genes following apparent nuclear translocation. This is consistent with a model in which LEDGF/p75 nuclear translocation occurs during early neuronal differentiation to trigger exit from NESC self-renewal and initiates entrance to the neuronal differentiation pathway. Moreover, transcriptional interaction with CREB metabolism is also consistent with this model, as this transcription factor has been widely implicated in regulation of neuronal development and differentiation. (See Fujioka et al., Neurosci 24:319-28 (2004); Murphy et al., Proc. Natl Acad Sci USA 94:1482-87 (1997); Crino et al., Proc Natl Acad Sci USA 95:2313-18 (1998); Riccio et al., Science 286:2358-61 (1999); Walton et al., J Neurosci Res 58:96-106 (1999); Walton et al., J. Neurochem 73:1836-42 (1999); Monti et al., Eur. J. Neurosci 16:1490-98 (2002); and Redmond et al., Neuron 34;999-1010 (2002)). A role for CREB has been characterized through in vivo and in vitro manipulations of CREB function. (See id.)

Increased nuclear LEDGF/p75 protein levels are associated with neuronal-oriented differentiation. As neuronal differentiation progresses, LEDGF/p75 redistributes to the cytosol, perhaps signaling final neuronal maturation. Such spatial-temporal regulation is compatible with a functional role of LEDGF/p75 as a transcriptional co-activator. However, sustained localization of LEDGF/p75 in the nucleus may indicate abnormal persistence of the progenitor cell state and increased tumorigenic potential.

Figure 6:
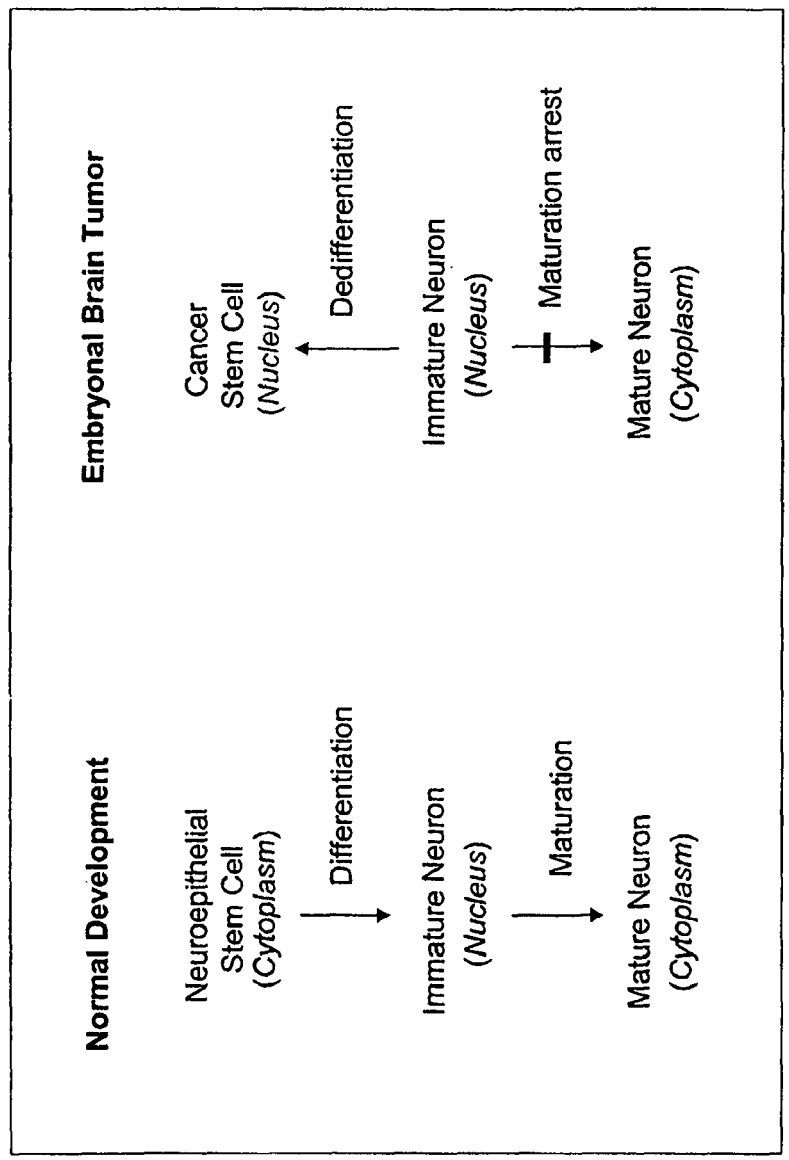
FIG. 6 is a schematic model showing the linear relationship between cell type and LEDGF/p75 expression in neurogenesis and in cancer. In this model, the nuclear accumulation of LEDGF/p75 controls stem cell differentiation and neuronal maturation.

Cancer cells frequently display immature or primitive morphology and deregulated expression of developmentally important genes. For example, medulloblastomas are aggressive pediatric brain tumors that are thought to originate in remnant EGL progenitor cells that fail to mature and inappropriately persist in the cerebellum. Transient translocation of LEDGF/p75 into the nucleus of EGL progenitor cells is a critical step for triggering granule cell neuronal differentiation during normal cerebellar development. Likewise, subsequent cytosolic relocation may be equally important in terminating the progenitor cell phenotype and/or stabilizing terminal differentiation of mature granule cells. However, persistent LEDGF/p75 localization in the nucleus may aberrantly alter the developmental program of gene expression, thereby inducing the tumor cell phenotype. (See FIG. 6). For example, hedgehog (Hh) and Wnt signaling pathways play central roles in stem cell renewal in normal tissue, whereas continuous activation is associated with tumorigenic transformation in a variety of human cancers.

LEDGF/p75 is differentially expressed and discretely localized within diverse mammalian brain tumors, such as, for example, medulloblastomas, meningioma, astrocytoma, glioblastoma multiforme, ependymoma, etc.). Specifically, nuclear expression is observed in medulloblastomas, cytoplasmic expression is observed in meningomas, and both nuclear and cytoplasma expression is observed in gliomas. LEDGF/p75 expression and/or subcellular localization patterns differ among these tumor types and appears to be cell type specific. Thus, LEDGF/p75 expression patterns can be used as a tumor biomarker for screening, identification, diagnosis, prognosis, staging, therapeutic stratification, response to treatment, and/or purification/isolation of tumor cells or tumor cell populations. Moreover, LEDGF/p75 measurements obtained from serum and/or CSF may be used as a peripheral biomarker of tumor screening, presence, burden, treatment response, etc.

Recently, HDGF has been shown to play a role in epithelial differentiation during intestinal development. HDGF mRNA is expressed prominently in early gut tissue but is substantially reduced after villous epithelial differentiation and dramatically increased in human colorectal cancer. (See Lepourcelet et al., Development 132:415-27 (2005)).

An apparently similar expression pattern for LEDGF/p75 has been observed during cerebellar development and in medulloblastoma. Thus, LEDGF/p75 plays a critical role as a key regulator of differentiation during normal and abnormal differentiation in the brain.

In addition, LEDGF/p75 protein expression is only detected in the cytoplasm of some cancer cells, such as colon cancer cells. Unlike LEDGF/p75 expression patterns in certain brain tumors, LEDGF/p75 is not detected in the nuclei of normal or cancerous epithelial cells. The positive frequency in colon cancer is about 26% (13/50). No positive staining in normal colon mucosa, and the positive intensity is weaker in colon tissues than in brain tumors. Moreover, granular staining can be seen in normal and cancerous epithelial cells, which may be associated with secreta of colon epithelial cells in normal and cancerous tissue.

LEDGF/p75 is Differentially Expressed by Cell Type in Fetal and Adult Human Brain.

LEDGF/p75 is highly expressed in the germinal neuroepithelium and cortical mantle of the developing fetal human brain and also in the subventricular zone (SVZ) of the adult human brain. (See Chylack et al., Exp Eye Res 79:941-48 (2004)). To determine the cell types exhibiting LEDGF/p75 expression in NESC-enriched brain regions, an immunohistofluorescence cell phenotyping survey was performed in fetal (26 weeks, see FIG. 1A-C) and aged adult human brain (89 years old, see FIGS. 1D-1E) using LEDGF/p75 immunohistochemistry combined with immunophenotyping using cell-specific markers for NESCs (nestin), newly-differentiated neurons (neural class III beta-tubulin, Tuj-1), and astrocytes (glial fibrillary acidic protein, GFAP). LEDGF/p75 and nestin co-localization within the cytoplasm of fetal brain cortical germinal matrix (see FIG. 1A) and in SVZ obtained from aged brain (see FIG. 1D) was observed.

All of the identified nestin-positive NESCs also demonstrated LEDGF/p75 immunopositivity. Moreover, presumptive newly-differentiated neurons within the fetal cortical mantle (see FIG. 1B) and adult SVZ (see FIG. 1E) co-immunostained for Tuj1 and LEDGF/p75 predominantly within the nucleus. GFAP positive astrocytes in the fetal cortical mantle (see FIG. 1C) and adult SVZ (see FIG. 1F) were devoid of LEDGF/p75 immunostaining. Taken together, these results indicate that LEDGF/p75 differentially localizes to the cytoplasm of NESCs and the nuclei of presumptive newly-differentiated neurons. LEDGF/p75 is largely absent from astrocytes in both fetal and adult human brain.

LEDGF/p75 is Differentially Expressed During Neurogliogenesis.

Figure 7:
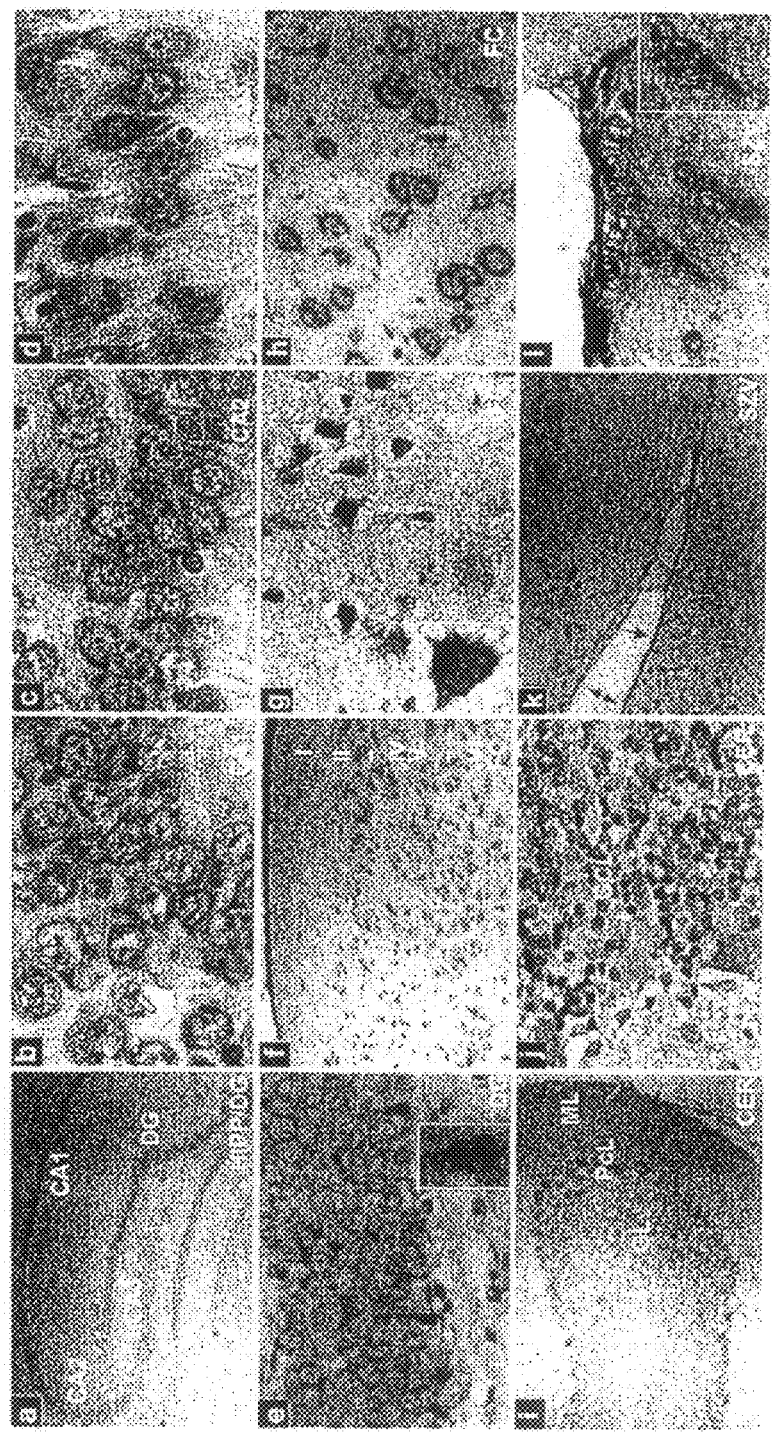
FIGS. 7A-L are a series of photomicrographs demonstrating that LEDGF/p75 localizes in the cytoplasm in the mature neurons in the adult rat brain. In these experiments, four-month old rat brain was immunostained using anti-LEDGF/p75 mAb.

In order to map LEDGF/p75 expression in the adult rat brain, a survey analysis of LEDGF/p75 immunostaining in four-month-old rats revealed modest cytoplasmic LEDGF/p75 immunopositivity throughout the brain and in ependymal cells lining the ventricles. (See FIG. 7). In the hippocampus, at low (see FIG. 7A) and high (see FIGS. 7B-7E) magnification, LEDGF/p75 is expressed in the cytoplasm in the neurons in CA1 (see FIG. 7B), CA2 (see FIG. 7C), CA3 (see FIG. 7D), and dentate gyrus (see FIGS. 7F-7H). Moreover, rat frontal cortex (FC) shows cytoplasmic expression of LEDGF/p75 in the layer IV (see FIG. 7G) with intense straining and the layer V (see FIG. 7H). Examination of rat cerebellum reveals lower expression of LEDGF/p75 in the granule layer (GL). (See FIGS. 7I-7J). Intense cytoplasmic LEDGF/p75 immunoreactivity in isolated subgranular zone (SGZ) cells in the dentate gyrus of four-month old rat brain was also observed. (See, e.g., FIGS. 2A and 7K-7L). These LEDGF/p75 SGZ cells also co-immunostained for nestin, thereby suggesting that LEDGF/p75 is expressed in NESC within the adult rat brain. This observation was confirmed in the adult human brain. (See FIG. 1D).

To investigate whether LEDGF/p75 is involved in neurogenesis, a rat primary NESC culture system (see Bonni et al., Science 278:477-83 (1997); and Johe et al., Genes Dev. 10:3129-40 (1996)) and immunohistofluorescence analysis were performed to study the temporal patterning of LEDGF/p75 expression during early NESC differentiation and neurogliogenesis. In primary NESC, LEDGF/p75 and nestin immunoreactivity co-localized with a prominent peri-nuclear distribution. (See FIG. 2B). Differentiating neurons demonstrated nuclear LEDGF/p75 immunoreactivity concomitant with expression of the neuronal marker, Tuj 1. (See FIG. 2C). By contrast, LEDGF/p75 immunoreactivity in newly-differentiated GFAP-positive astrocytes was markedly diminished or absent altogether. (See FIG. 2D).

Three different techniques (immunohistofluorescence combined with confocal photomicroscopy (see FIG. 2E), anti-LEDGF/p75 immunogold electron microscopy (IEM, see FIGS. 2F-2G), and cellular fractionation combined with western blotting) were utilized to confirm differential cell phenotype-specific LEDGF/p75 subcellular localization. (See FIG. 2H). Thus, these data indicate that there is a LEDGF/p75 cytoplasmic-to-nuclear translocation during early NESC-derived neurogenesis.

Figure 2:
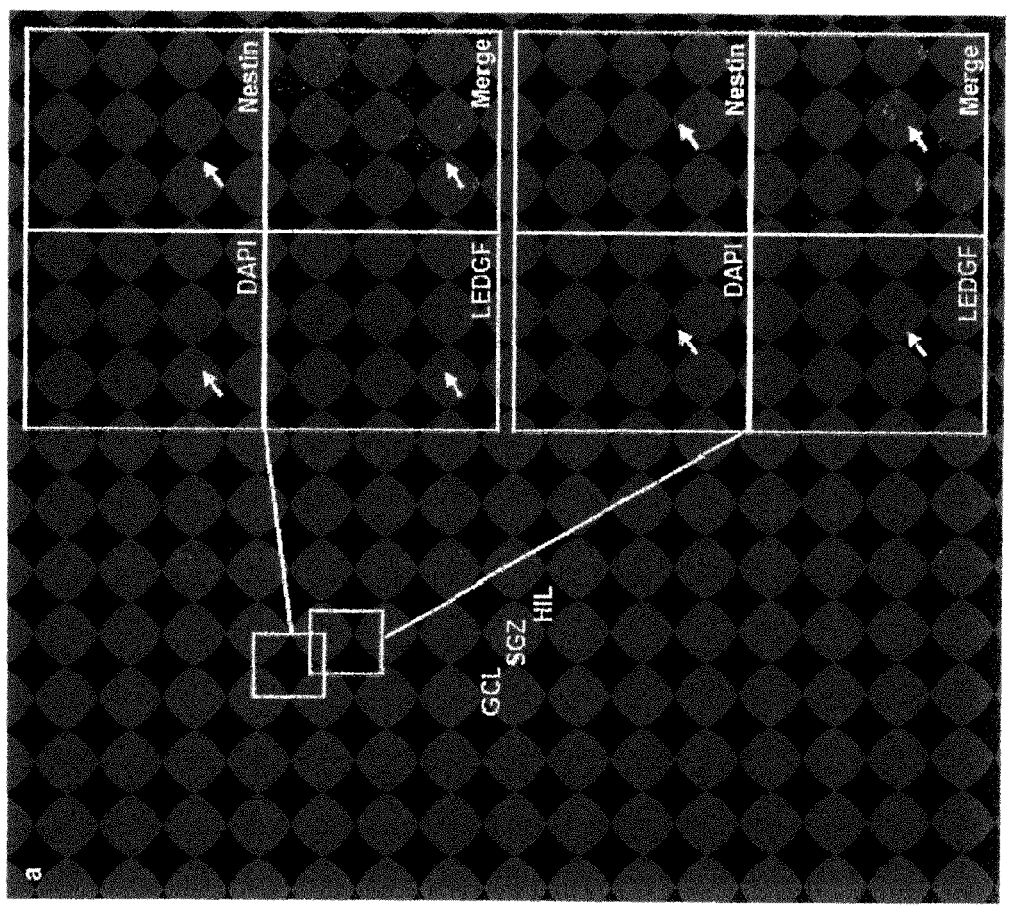
FIGS. 2A-J are a series of photomicrographs demonstrating that LEDGF/p75 mRNA and protein expression and localization differ within neuroepithelial stem cell (NSC), neuron (NEU), and astrocyte (AST) differentiation.
Figure 2:
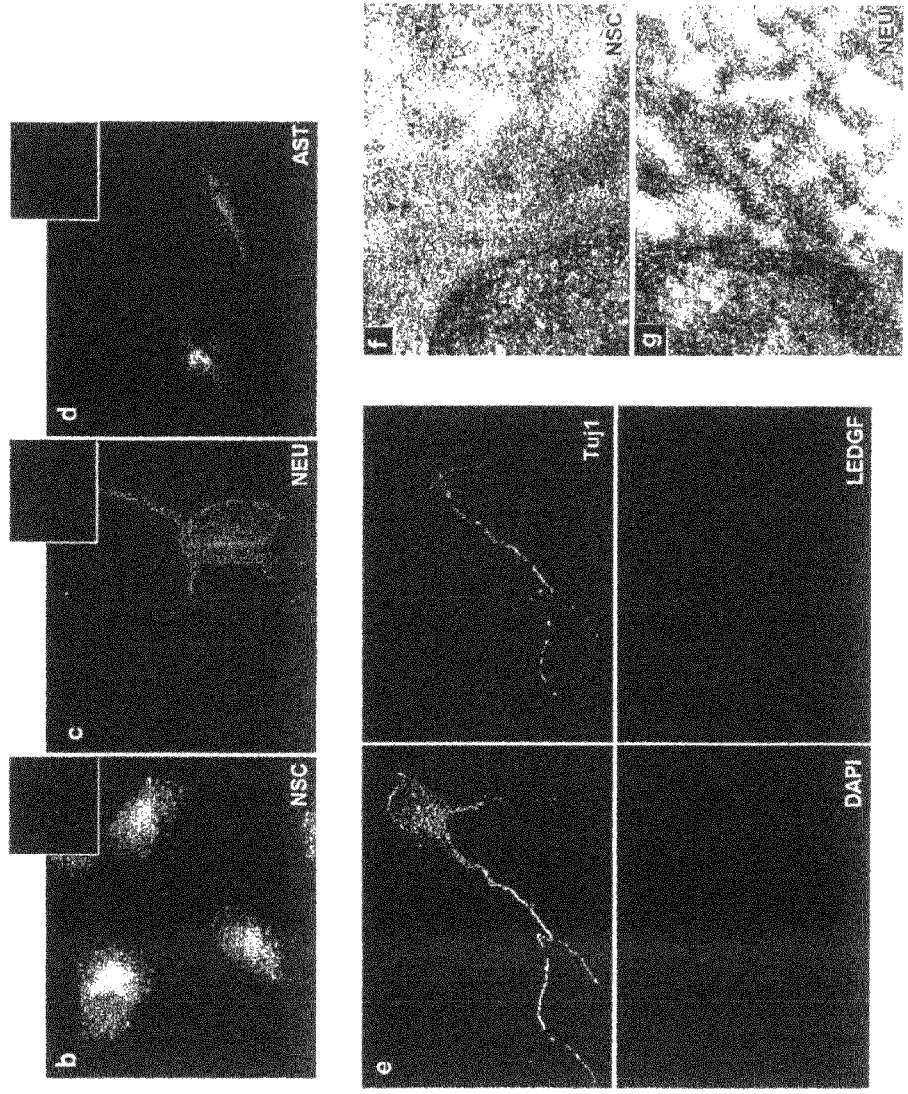

LEDGF/p75 mRNA is slightly reduced without any change in protein levels during early neuronal differentiation. By contrast, both LEDGF/p75 mRNA and LEDGF/p75 protein levels are reduced during astrocytic differentiation. (See FIGS. 2I-2J). As shown in FIG. 2J, after three days of differentiation, lysates of newly differentiated neurons and astrocytes were immunomodulated for LEDGF/p75 with βin used as a loading control. Thus, LEDGF/p75 expression and localization differ during neuron and astrocyte differentiation. Similar findings have also been observed in human brain. (See FIG. 1A-1F).

F/p75 Knockdown Blocks Neurogenesis and Induces Astrogliogenesis.

LEDGF/p75 is expressed in human fetal germinative neuroepithelium and adult SVZ. Both of these brain regions are enriched in NESCs and support neurogliogenic differentiation. (See Buc-Caron, Neurobiol Dis 2:37-47 (1995); Eriksson et al., Nat Med 4:1313-17 (1998); Kirschenbaum et al., Cereb Cortex 4:576-89 (1994); and Bernier et al., Neurosci Res 37:67-78 (2000)). Moreover, differential LEDGF/p75 expression and subcellular localization that follows a cell phenotype-specific pattern has been observed, thereby suggesting a regulatory role for this transcription factor in neurogliogenesis.

A lentiviral RNA interference system (see Rubinson et al., Nat Genet 33:401-06 (2003) was employed to study the effect of LEDGF/p75 knockdown during NESC-derived neurogenesis. Two different regions of the LEDGF/p75 gene were used as target sequences for constructing LEDGF/p75 shRNA vectors. Typical infection rates using these vectors in primary rat E14 neocortical NESC cultures were greater than 95% as evidenced by GFP expression. At passage 3 (E14+P3), immunocytochemical analysis of rat primary neocortical cultures demonstrated co-localization of LEDGF/p75 and nestin, while essentially none (<0.001%) of the cells expressed Tuj 1 or GFAP. These results indicate that essentially all of the E14+P3 cells were NESCs.

Three days post-transduction (E14+P3), LEDGF/p75 shRNA-transduced NESC primary cultures were examined for LEDGF/p75 expression by immunocytochemistry, RT-PCR, and immunoblotting. (See FIGS. 3A-3B). LEDGF/p75 expression was markedly decreased in undifferentiated NESC (E14+P3) cultures treated with either of two LEDGF/p75 shRNA lentiviruses (rank order: LEDGF/p75i2>LEDGF/p75i1>Ctrl lentivirus). To assess the functional significance of LEDGF/p75 knockdown, transduced NESC (E14+P3) cultures with either of the two shRNA lentiviruses or a control lentivirus for three days, then induced neuronal differentiation.

LEDGF/p75i lentivirus treatment resulted in a significantly blocked or markedly reduced NESC-derived newly-differentiated Tuj 1-positive neurons as compared to cultures infected with control lentivirus. (See FIG. 3C). Tuj 1-positive neurons were significantly decreased by both LEDGF/p75i lentiviruses, with the greatest impact mediated by LEDGF/p75i2. Primary NESC cultures treated with LEDGF/p75i2 revealed few Tuj 1-positive neurons within a large portion of nestin-positive NESCs at day one and day four after neuronal induction. (See FIG. 3D). Quantitative assessment of these cultures by cell phenotype showed a significant reduction in newly-differentiated Tuj 1-positive neurons relative to nestin-positive NESCs following LEDGF/p75i treatment.

These results show that the differentiation of NESCs into newly-differentiated neurons is regulated by LEDGF/p75 expression. Conversely, lentiviral LEDGF/p75 RNAi knockdown in NESC (E14+P3) cultures markedly induced NESC-derived astrocytic differentiation. (See FIGS. 3E-3F). These results also indicate that LEDGF/p75 expression is necessary for NESC-derived neuronal differentiation and that decreasing LEDGF/p75 expression in NESCs promotes astrocytic differentiation. Moreover, these LEDGF/p75 knockdown NESC-derived astrocytic cultures showed aberrant polymorphic cellular morphology and an apparent loss of contact inhibition.

LEDGF/p75 Regulates CREB Expression and Ser-133 Phosphorylation.

CREB is a gene that is expressed in NESC. It is a key mediator of gene expression in developing neurons in both its native and phosphorylated states. (See Lonze et al., Neuron 35:605-23 (2002)). As noted, LEDGF/p75 has been reported to bind to stress-related regulatory elements (STREs). (See Singh et al., Biochem Biophys Res Commun 283:943-55 (2001)). The CREB promoter contains two such sites at nucleotides −1138 through −1133 and nucleotides −937 through −932.

Figure 4:
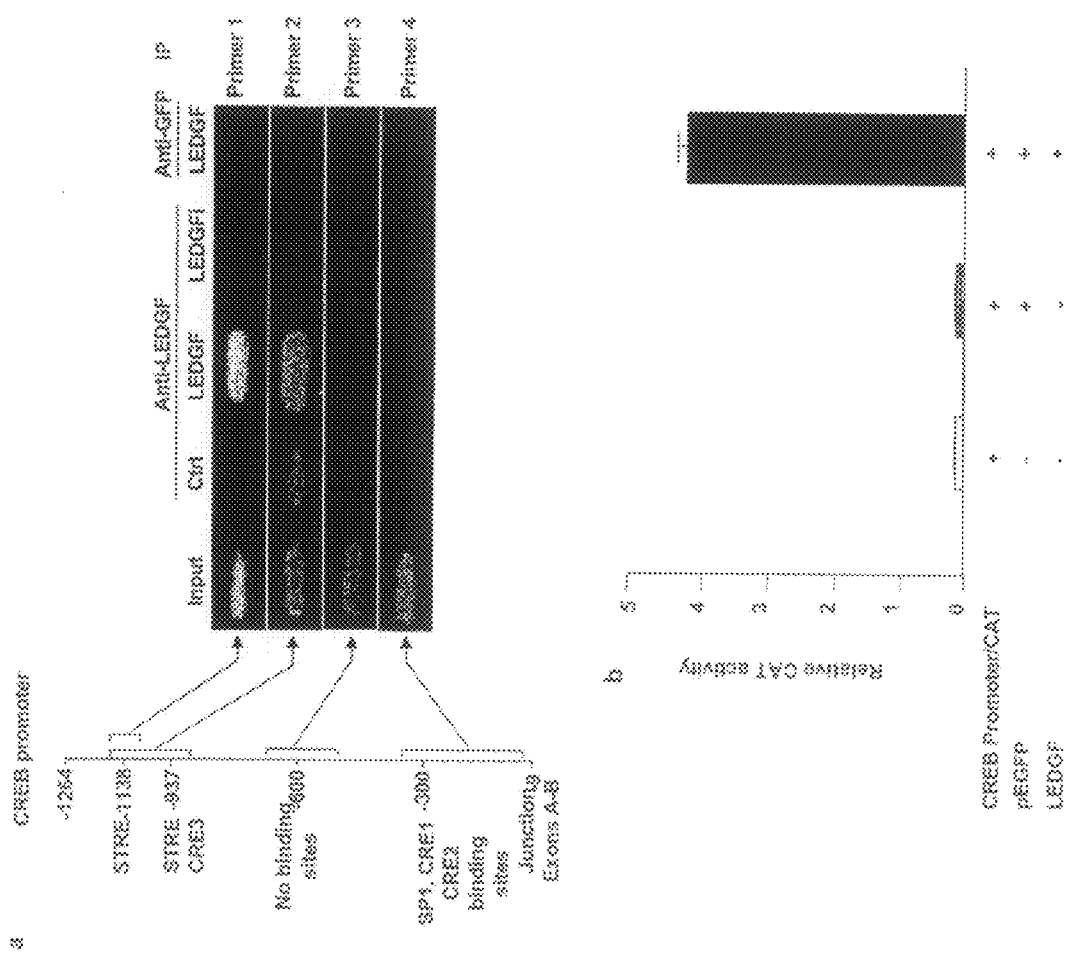
FIG. 4A is a ChIP analysis of LEDGF/p75 binding to the CREB promoter in SY5Y cells (right-hand diagram) and a schematic representation of relevant regions of the relevant regions of the CREB promoter (left-hand diagram).
FIG. 4B is a graph demonstrating relative CAT activity when the CREB promoter fused to a CAT reporter was transfected alone, or co-transfected with pGFP, or with pEGFP and LEDGF/p75 plasmids into SY5Y cells, respectively.
FIG. 4C is a Western blot analysis with CREB-p at SER 133 antibody that demonstrates that CREB activation was induced in early neuronal differentiation.
FIG. 4D is a Western blot analysis showing that neuronal differentiation is reduced by LEDGF/p75 or CREB oligonucleotides siRNA. Together.
FIG. 4E is a Western blot analysis showing that overexpression of LEDGF/p75 increases CREB and neuronal Tuj1 expression, where the blot was probed with GAPDH as loading control, and the results represent four independent experiments.

Chromatin immunoprecipitation (ChIP) analyses demonstrated LEDGF/p75 binding to the endogenous CREB promoter in SY5Y neuroblastoma cells under basal conditions. (See FIG. 4A). SY5Y cells that overexpress LEDGF/p75 exhibited increased binding of LEDGF/p75 to the CREB promoter. By contrast, LEDGF/p75 binding to the CREB promoter was not detected in SY5Y cells following RNAi-mediated LEDGF/p75 knockdown. Thus, LEDGF/p75 appears to bind to the CREB promoter at one or both of the STRE sites. SY5Y cells engineered to express a CAT reporter gene driven by a large region of the human CREB promoter were used to show that LEDGF/p75 over-expression stimulated CAT expression driven by the CREB promoter. (See FIG. 4B). Therefore, CREB is a direct transcriptional target of LEDGF/p75.

The primary NESC (E14+P3) culture system was used to assay for CREB protein expression and Ser-133 phosphorylation activation during NESC-derived neuronal differentiation. The level of total CREB protein remained unchanged in cultures containing NESCs or NESC-derived neurons. However, CREB activation via Ser-133 phosphorylation was significantly and transiently increased within 24 hours after neuronal induction. (See FIG. 4C). Thus, LEDGF/p75 knockdown in E14+P3 NESCs resulted not only in the expected inhibition of neuronal differentiation, but also in a reduction in total CREB protein and Ser-133 phosphorylated CREB protein. (See FIG. 4D).

Conversely, LEDGF/p75 overexpression in NESCs promoted neuronal differentiation and also CREB protein expression. LEDGF/p75 overexpression also consistently and progressively increased total CREB protein expression throughout differentiation, while CREB phosphorylation at Ser-133 exhibited a substantial but transient increase that peaked at ~24 hours. (See FIG. 4E). Thus, LEDGF/p75 appears to regulate NESC-derived neurogenesis by direct transcriptional control of CREB expression and activation and by post-translational processing via specific phosphorylation.

LEDGF/p75 and CREB Expression in Normal Cerebellar Development and in Medulloblastoma Many developmentally down-regulated genes are inappropriately re-expressed in tumors. (See Lepourcelet et al., Development 132: 415-27 (2005)). Thus, LEDGF/p75 might be expressed in a common embryonal brain tumor, medulloblastoma, which is thought to arise from aberrant differentiation of remnant external granule cell (EGL) or subventricular zone (SVZ) neuroepithelial progenitor cells residing within the cerebellum. Analysis of a human brain tumor array found strong nuclear LEDGF/p75 immunopositivity in 15 of 15 medulloblastomas that was not observed in control specimens. A second series of medulloblastoma specimens was independently examined using immunohistochemistry, and intense nuclear LEDGF/p75 immunostaining was observed. (See FIGS. 5A-5B). LEDGF/p75 immunostaining was not observed in vascular endothelia cells in areas adjacent to tumor. (See FIG. 5B).

LEDGF/p75 expression during normal human cerebellum development was also examined. At 32 weeks (see FIG. 5C), the developing fetal human cerebellum reveals a well-developed EGL that is enriched in granule neuron progenitors. These EGL progenitor cells exhibited intense LEDGF/p75 immunopositivity that exclusively localized to the cytoplasm. (See FIG. 5D). Graded expression of LEDGF/p75 in granule neuron precursors along the EGL maturation migratory pathway, from the outer EGL (OEGL) to the inner EGL (iEGL) subregions was observed. (See FIG. 5E). Likewise, strong nuclear staining in the granule cells in the internal granule cell layer (IGL) in fetal brain has also been observed. (See FIG. 5F).

During maturation, the EGL depopulates as the progenitor cells migrate to the granule cell layer (GCL). Here, the former EGL progenitor cells terminally differentiate into the mature granule cell neurons that distinguish this layer of the adult cerebellum. Within the adult (age 18) GCL, LEDGF/p75 expression was weak. (See FIGS. 5G-5H). Moreover, LEDGF/p75 immunostaining in these mature, terminally differentiated GCL neurons was restricted to the cytoplasm. Therefore, the LEDGF/p75 expression pattern in medulloblastoma is more like that in the developing fetal cerebellum, in which LEDGF/p75 is primarily localized in the nuclei of immature neurons.

Figure 5:
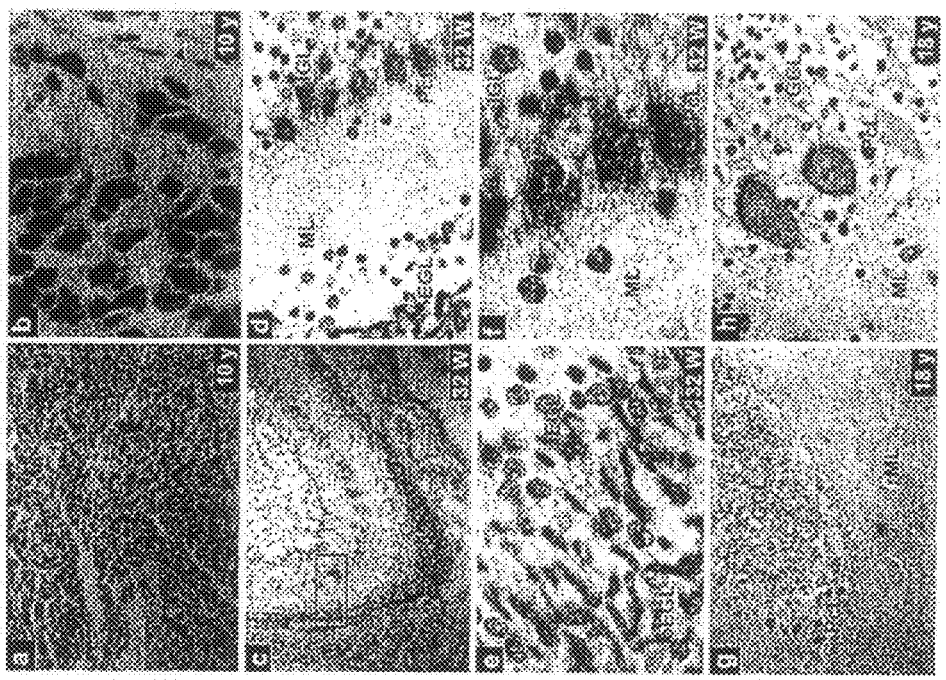
FIGS. 5A-P are a series of photomicrographs showing the differential expression level and pattern of LEDGF/p75 and CREB in the normal development of cerebellum tissues and medulloblastoma. The results shown are representative images from the brain tumor array, four individual medulloblastoma cases, and four normal cerebellum tissues.
Figure 5:
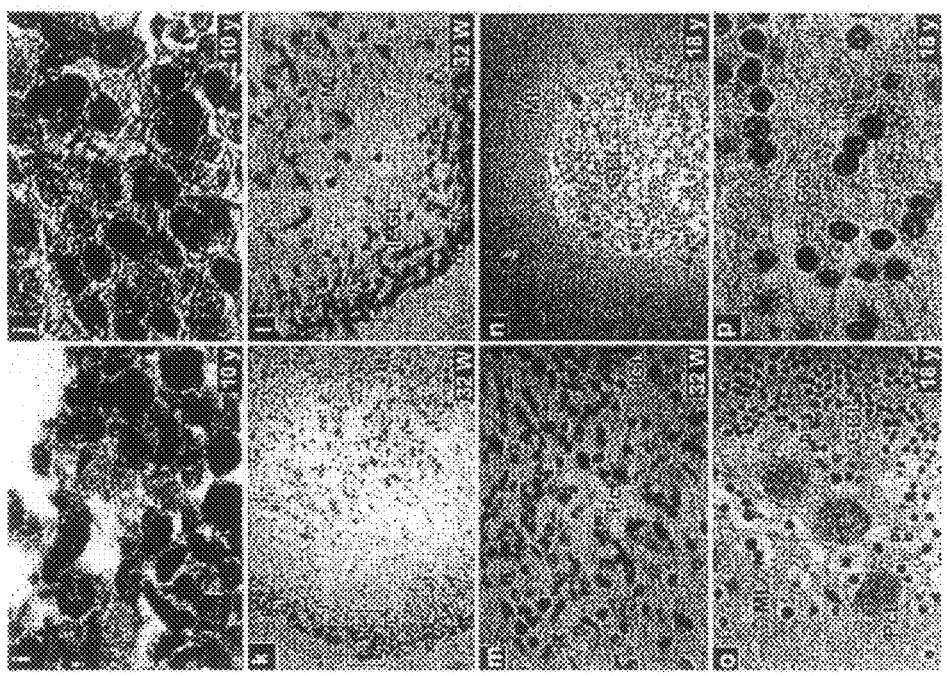

In this context, there is a marked increase in both total CREB protein expression and Ser-133 phosphorylation in medulloblastoma (see FIGS. 5I-5J) relative to normal human adult brain (see FIGS. 5N-5P). A similar pattern of intense nuclear CREB immunopositivity and Ser-133 phosphorylation in the developing fetal cerebellum has also been observed. (See FIGS. 5K-5M). Thus, increased expression and nuclear localization of LEDGF/p75 and CREB correlated with human medulloblastoma and discriminated this pediatric embryonal brain tumor from normal cerebellum as well as from other brain tumors such as meningioma, a non-embryonic tumor.

LEDGF/p75 in Stem Cells

Localization of LEDGF/p75 was studied in human fetal and adult brain. LEDGF/p75 was found to be expressed in the fetal and adult human brain and subcellularly localized in cytoplasm of Nestin-positive cells and the nucleus of Tuj-1 positive cells. Differential expression and localization of LEDGF/p75 was evaluated in NESCs, newly differentiated neuron and astrocytic cell cultures. LEDGF/p75 was found to be expressed in the cytoplasm of neural stem cells and the nucleus of newly differentiated neurons as determined by immunostaining and subcellular fractionation followed by Western Blot analysis. The expression of LEDGF/p75 was found to be decreased in newly differentiated astrocytes as determined by immunostaining and real-time RT-PCR. LEDGF/p75 knockdown using and RNAi system was found to block neuronal differentiation. Inhibition of LEDGF/p75 was associated with a significant reduction in neuronal differentiation from first differentiation day (and over 6 days) compared with a control. LEDGF/p75 regulates neuronal differentiation in a CREB-dependent mechanism.

Based on the foregoing data, LEDGF/p75 is also useful in methods for identification, localization, isolation, purification, and differentiation of stem cells such as human stem cells. LEDGF/p75 is expressed in stem cell progenitor cells in prenatal and postnatal mammalian organisms and is also used to identify, classify, and stage stem cell related tumors as well as to evaluate treatment, stratification/responsivity to therapeutic intervention.

The invention is further illustrated by the following non-limiting examples.

EXAMPLES

Example 1

Cell Culture and Transfection

Primary NESC cultures were prepared as previously described. (See Bonni, et al., Science 278:477-83 (1997); and Johe, et al., Genes Dev 10:3129-40 (1996)). Briefly, cortical cups were dissected from frontal cortices harvested from Long Evans rat E14 embryos, mechanically triturated, and washed in HBSS (Hanks' Buffered Saline Solution). Pellets were presuspended in Basal Medium Eagle (Sigma) supplemented with 1×N2 supplement (Invitrogen), 3.5% 1M glucose, 1% penicillin/streptomycin/glutamine (Invitrogen), and 20 ng/mL bFGF (R&D) and plated on polyornithine and fibronectin-coated surfaces.

Cells were treated with 10 ng/ml bFGF every 24 hours and passaged approximately every three days. Cells were used at passage three for all experiments. SY5Y cells were cultured in Dulbecco's modified Eagle's medium (DMEM) containing 10% FBS, penicillin-streptomycin (Invitrogen). LEDGF/p75 siRNA Oligo (siRNA duplex) was synthesized from (DHARMACON). Cells were transfected with CREB SMAPT pool siRNA reagent (Upstate), Control Non-Targeting siRNA and LEDGF/p75 siRNA Oligo by TransIT-TKO transfection reagent (Mirus). Full length coding sequence of LEDGF/p75 was subcloned into pcDNA3.1 D/V5-His-TOPO vector (Invitrogen), pcDNA-LEDGF/p75 confirmed by sequencing and CREB promoter plasmids transfections were performed with Fugene6 (Roche) according to the manufacturer's protocol.

For ChIP and promoter assay experiments, a GFP cDNA, pGFP empty plasmid (Clontech) was co-transfected with LEDGF/p75 plasmid or/and CREB promoter plasmid to assess the transfection efficiency. The reliability of co-transfection of these plasmids was assessed to be >90% by observation of the presence of GFP fluorescence.

Example 2

Short Hairpin RNAs (shRNAs)

pLL3.7, a lentiviral shRNA vector, was provided by the MIT Cancer Institute. The annealed oligonucleotide sequences are listed in Table 5.

TABLE 5

| Primer | Sequence | SEQ ID NO: |
|---|---|---|
| ChIPs and transcript analysis on CREB promoter: | | |
| Primer 1_for | AGA CTT GAA ACC CCA AGG AG | 1 |
| Primer 1_rev | TTC TTT CCT CAG CCT GTT TTC | 2 |
| Primer 2_for | AGA CTT GAA ACC CCA AGG AG | 3 |
| Primer 2_rev | TGG CCC CGA TAC TGT GGC AC | 4 |
| Primer 3_for | ACC CGT CCC CAC GGG GGT CCC | 5 |
| Primer 3_rev | GAA CTT TCC GAC GCC GCC GGG A | 6 |
| Primer 4_for | AGA AAC CCG AAG GTC TTC GGC | 7 |
| Primer 4_rev | GGA TCT CGC TGG AGT TTT ATT | 8 |

TABLE 5-continued

| Primer | Sequence | SEQ ID NO: |
|---|---|---|
| RT-PCR on rat LEDGF/p75 gene: | | |
| RT-PCR_for | GCAGCAACCGCTTCTAATGT | 9 |
| RT-PCR_rev | CCTTTTGGCCTTCTTCCTCT | 10 |
| Real Time RT-PCR on rat LEDGF/p75 gene: | | |
| RT-PCR_for | CTC GCG ATT TCA AAC CTG GAG A | 11 |
| RT-PCR_rev | TTT GGT TTG CCA TAC TTT TCC T | 12 |
| 18S ribosomal subunit: | | |
| RT-PCR_for | ACG GAA GGG CAC CAC CAGG A | 13 |
| RT-PCR_rev | CAC CAC CAC CCA CGG AAT CG | 14 |
| Construction of the pcDNA-LEDGF/p75: | | |
| pcDNA-LEDGF/p75_for | CGGAAACATGACTCGCGATTTC | 15 |
| pcDNA-LEDGF/p75_rev | GTATGTCAACCTAGTTATCTAGT | 16 |
| Construction of the pLL-LEDGF/p75 shRNA: | | |
| shRNAi 1_for | TGCGAGAAACATCAATGGATTTCAAGAGAATCCATTGATGTTTCTCGCTTTTTGGAAAC | 17 |
| shRNA 1_rev | TCGAGTTTCCAAAAAGCGAGAAACATCAATGGATTCTCTTGAAATCCATTGATGTTTCTCGCA | 18 |
| shRNA 2_for | TGAAGGAAAGAAGCCAGAAGTTCAAGAGACTTCTGGCTTCTTTCCTTCTTTTTGGAAAC | 19 |
| shRNAi 2_rev | TCGAGTTTCCAAAAAGAAGGAAAGAAGCCAGAAGTCTCTTGAACTTCTGGCTTCTTTCCTTCA | 20 |
| LEDGF/p75 siRNA Oligo: | | |
| siRNA Target Seq: | AAAGACAGCAUGAGGAAGCGA | 21 |
| siRNA Sense Seq: | AGACAGCAUGAGGAAGCGAUU | 22 |
| siRNA Antisense Seq: | UCGCUUCCUCAUGCUGUCUUU | 23 |

The 18-nucleotide LEDGF/p75 target sequence was ligated into the pLL3.7 vector and confirmed by sequencing. Lentiviral generation and titre concentration were conducted according to published methods. (See Rubinson et al., Nat Genet 33:401-6 (2003)).

Example 3

Chromatin Immunoprecipitation (ChIP) Analysis

ChIP assay was conducted using a commercial kit (Upstate) on cell lysate extracted from SY5Y cells (LEDGF/p75-overexpressing, or LEDGF/p75 knockdown) in accordance with the manufacturer's protocol. SY5Y cells were transiently transfected with pcDNA with pEGFP, or LEDGF/pcDNA with pEGFP plasmids for 36 hours, respectively, or infected with LEDGF/p75i lentivirus for 3 days before cells were cross-linked with formaldehyde for ChIP analysis. Independent IP reactions were carried out with LEDGF/p75 antibody (BW 095, 1:200) and IP control reactions with anti-GFP antibody as a negative control, respectively. ChIP DNA were PCR-amplified using primers covering potential LEDGF/p75 binding sites within the indicated regulatory regions. Purified input chromatin was also used to perform parallel PCRs with all primer pairs. Primers for the human CREB 5' UTR promoter region are listed in Table 5.

Example 4

Immunofluorescence (IFC) and Immunohistochemistry (IHC)

NESCs (E14+P3) were infected by control or two different LEDGF/p75i lentiviruses for 3 days and then induced towards neuronal or astrocytic differentiation for the indicated days followed by immunofluorescence. Cells were double stained combining differential markers with LEDGF/p75 and DAPA. Immunostaining was performed as described previously. (See Chylack, et al., Exp Eye Res 79:941-8 (2004)). The antibodies that were used included: neuronal class III β-tubulin (Tuj-1) (1:400, Covance), anti-nestin (1:200, BD), anti-GFAP (1:400, BD), anti-CREB (1:500, Cell Signaling Technology), anti-phospho-CREB Ser133 (1:500, Cell Signaling Technology), anti-LEDGF/p75 polyclonal (1:2000, BW 095), and anti-LEDGF/p75 monoclonal (1:50, BW108) antibodies developed in the laboratory.

Example 5

Western Blot

Western blotting was performed according to standard protocols. The antibodies that were used included: anti-C-terminal LEDGF/p75 (BW 095, 1:2000), anti-Tuj 1(1:1000), anti-GFAP (1:1000), anti-CREB (1:2000, Upstate), anti-phospho-CREB (1:1000, Upstate). Immunoblot quantification was performed by using ImageJ software. Subcellular fractionation was conducted by differential detergent fractionation method as previously described. (See Simpson, Proteins and Proteomics: A Laboratory Manual. Cold Spring Harbor, N.Y.: Cold Spring Harbor Laboratory Press (2003)). The total cellular protein and the fraction of cytoplasmic (Cyto), membrane (Mem), and nuclear (Nuc) were extracted from the NESCs and neurons at three days differentiation and immunoblotted with anti-LEDGF/p75.

Example 6

Brain Tumors Micro-Array

The brain tumor tissue micro-array was constructed at Cell Signaling Technology (CST) following core selection by a CST pathologist. The tissue micro-array was stained following standard manual IHC procedures including antigen retrieval with citrate buffer and detection with the Vector ABC kit and NovaRed substrate. The LEDGF pAb was used at a concentration of 1:1000. The CREB protein was detected using the CST rabbit monoclonal antibody number 9197 at a concentration of 0.25 μg/ml.

Example 7

Real-Time RT-PCR

Quantitative RT-PCR was performed by reverse transcription of total cellular RNA. Total cellular RNA was treated with RNase-free DNase and purified with RNeasy system (Qiagen), according to the manufacturer's instructions. The RNA samples normalized for concentration were prepared for first First-strand by using the Superscript First Strand cDNA synthesis system (Invitrogen). For quantitative PCR, genes were amplified in the presence of SYBR-green and incorporated fluorescence was measured and normalized to amplification of the 18S ribosomal unit. Amplification of LEDGF/p75 and 18S ribosomal subunit was achieved using the sequences shown in Table 5.

Example 8

Reporter Gene Assay

CAT activity was measured by ELISA (Roche) according to the manufacturer's instructions. The CREB promoter plasmid was gift from Dr. J. Habener of Massachusetts General Hospital. For all assays, cells were lysed two days after transfection.

Example 9

Statistical Analysis

Statistical comparisons among groups were made using one-way analysis of variance. Student's t test was used for the post hoc comparison of individual mean values. p values *$p<0.01$, **$p<0.001$ were considered statistically significant. Data shown represent the means±S.E.

OTHER EMBODIMENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

---

What is claimed is:

1. A method for diagnosing a tumor in the central nervous system of a mammal comprising contacting cerebrospinal fluid from said mammal with a reagent that binds to LEDGF/p75 under conditions sufficient to form a LEDGF/p75 reagent complex and detecting said complex, wherein elevation of LEDGF/p75 compared to a normal control level as measured by the presence of said complex indicates that said mammal has a tumor.

2. The method of claim 1, wherein the tumor is located in the CNS, of the mammal.

3. The method of claim 2, wherein the tumor is a brain tumor selected from the group consisting of medulloblastoma, meningioma, astrocytoma, glioblastoma multiforme, and ependymoma.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1

```
agacttgaaa ccccaaggag                                                   20

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
ttctttcctc agcctgtttt c                                                 21

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 3
agacttgaaa ccccaaggag                                                   20

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
tggccccgat actgtggcac                                                   20

<210> SEQ ID NO 5
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 5
acccgtcccc acggggtcc c                                                  21

<210> SEQ ID NO 6
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 6
gaactttccg acgccgccgg ga                                                22

<210> SEQ ID NO 7
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 7
agaaacccga aggtcttcgg c                                                 21

<210> SEQ ID NO 8
<211> LENGTH: 21
<212> TYPE: DNA
<213> ORGANISM: Artificial Sequence
<220> FEATURE:
```

-continued

<223> OTHER INFORMATION: Chemically Synthesized

<400> SEQUENCE: 8
ggatctcgct ggagttttat t          21

<210> SEQ ID NO 9
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 9
gcagcaaccg cttctaatgt          20

<210> SEQ ID NO 10
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 10 cctttggcc ttcttcctct          20

<210> SEQ ID NO 11
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 11
ctcgcgattt caaacctgga ga          22

<210> SEQ ID NO 12
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 12
tttggtttgc catactttc ct          22

<210> SEQ ID NO 13
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 13
acggaagggc accaccagga          20

<210> SEQ ID NO 14
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 14
caccaccacc cacggaatcg          20

<210> SEQ ID NO 15

<211> LENGTH: 22
<212> TYPE: DNA
<213> ORGANISM: Artificial Sequence
<220> FEATURE:
<223> OTHER INFORMATION: Chemically Synthesized

<400> SEQUENCE: 15
cggaaacatg actcgcgatt tc                                            22

<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 16
gtatgtcaac ctagttatct agt                                           23

<210> SEQ ID NO 17
<211> LENGTH: 59
<212> TYPE: DNA
<213> ORGANISM: Artificial Sequence
<220> FEATURE:
<223> OTHER INFORMATION: Chemically Synthesized

<400> SEQUENCE: 17
tgcgagaaac atcaatggat tcaagagaa tccattgatg tttctcgctt tttggaaac     59

<210> SEQ ID NO 18
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 18
tcgagtttcc aaaaagcgag aaacatcaat ggattctctt gaaatccatt gatgtttctc   60
gca                                                                 63

<210> SEQ ID NO 19
<211> LENGTH: 59
<212> TYPE: DNA
<213> ORGANISM: Artificial Sequence
<220> FEATURE:
<223> OTHER INFORMATION: Chemically Synthesized

<400> SEQUENCE: 19
tgaaggaaag aagccagaag ttcaagagac ttctggcttc tttccttctt tttggaaac    59

<210> SEQ ID NO 20
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 20
tcgagtttcc aaaaagaagg aaagaagcca gaagtctctt gaacttctgg cttctttcct   60
tca                                                                 63

<210> SEQ ID NO 21
<211> LENGTH: 21
<212> TYPE: RNA
<213> ORGANISM: Artificial Sequence
<220> FEATURE:

<223> OTHER INFORMATION: Chemically Synthesized

<400> SEQUENCE: 21
aaagacagca ugaggaagcg a                                              21

<210> SEQ ID NO 22
<211> LENGTH: 21
<212> TYPE: RNA
<213> ORGANISM: Artificial Sequence
<220> FEATURE:
<223> OTHER INFORMATION: Chemically Synthesized

<400> SEQUENCE: 22
agacagcaug aggaagcgau u                                              21

<210> SEQ ID NO 23
<211> LENGTH: 21
<212> TYPE: RNA
<213> ORGANISM: Artificial Sequence
<220> FEATURE:
<223> OTHER INFORMATION: Chemically Synthesized

<400> SEQUENCE: 23
ucgcuuccuc augcugucuu u                                              21

<210> SEQ ID NO 24
<211> LENGTH: 1677
<212> TYPE: DNA
<213> ORGANISM: Homo sapiens

<400> SEQUENCE: 24

```
gaattcgcgg ccgccccgcg ccgccgcatc tcctcgccgc ctcccgggct tcggaccccc      60
ggtctcgccc ccgaaacatg actcgcgatt tcaaacctgg agacctcatc ttcgccaaga     120
tgaaggttta tccccattgg ccagctcgag tagacgaagt tcctgatgga gctgtaaagc     180
cacccacaaa caaactaccc attttctttt ttggaactca tgagactgct tttttaggac     240
caaaggatat atttccttac tcagaaaata ggaaaagta tggcaaacca ataaaagaa      300
```
(Note: the above line 300 appears to read "ggaaaagta tggcaaacca aataaaagaa")
```
aaggttttaa tgaaggttta tgggagatag ataacaatcc aaaagtgaaa ttttcaagtc     360
aacaggcagc aactaaacaa tcaaatgcat catctgatgt tgaagttgaa gaaaaggaaa     420
ctagtgtttc aaaggaagat accgaccatg aagaaaagc cagcaatgag gatgtgacta     480
aagcagttga cataactact ccaaaagctg ccagaagggg gagaaagaga aaggcagaaa     540
aacaagtaga aactgaggag gcaggagtag tgacaacagc aacagcatct gttaatctaa     600
aagtgagtcc taaaagagga cgacctgcag ctacagaagt caagattcca aaaccaagag     660
gcagacccaa aatggtaaaa cagccctgtc cttcagagag tgacatcatt actgaagagg     720
acaaaagtaa gaaaagggg caagagggaa acaacctaa aaagcagcct aagaaggatg     780
aagagggcca gaaggaagaa gataagccaa gaaagagcc ggataaaaaa gaggggaaga     840
agaagttga atcaaaaagg aaaaatttag ctaaacagg ggttacttca acctccgatt     900
ctgaagaaga aggagatgat caagaaggtg aaaagaagaa aaaggtgggg aggaactttc     960
agactgctca cagaaggaat atgctgaaag gccaacatga gaaagaagca gcagatcgaa    1020
aacgcaagca gaggaacaa atggaaactg agcaccaaac aacatgtaat ctacagtaat    1080
aaaaatata tctcattttg ggctcaaagc attaatccag ttactgaaaa gagaatacaa    1140
gtggagcaaa caagagatga agatcttgat acagactcat tggactgaat ttccccttc    1200
cccccatgat ggaagaatgt tcagattcta aattgaggac ttcattatta atggcattac    1260
```

```
tgtgttatga ttaacaaatt tcttgtaagg tacacactac atactaaggt cggccatcat   1320
tccgtttttt ttttttttt tttttttaac caagcttaaa atgaagctta aaatgaagct   1380
ttgtgtttga agtaataac aagctcagac gaagatggtg gttgtacatt attcatctag   1440
aaaatataaa aattcatttt gttttgaagc tagttattaa actggaatag cagttatatc   1500
cctgagaatg gggcccttct cttgacattc cttttgttgt ttaattcttt agaatcttaa   1560
taaatgtttt tttaatcctg agagattaaa cagtagtaga cttgttaaga atgaaactgt   1620
aaccaaaatt ttaaaataaa gttttttta aaaaaaaaaa aaaaaaaaaa aaaaaaa      1677
```

<210> SEQ ID NO 25
<211> LENGTH: 530
<212> TYPE: PRT
<213> ORGANISM: Homo sapiens

<400> SEQUENCE: 25

```
Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205

Asp Ile Ile Thr Glu Glu Asp Lys Ser Lys Lys Gly Gln Glu Glu
    210                 215                 220

Lys Gln Pro Lys Lys Gln Pro Lys Lys Asp Glu Glu Gly Gln Lys Glu
225                 230                 235                 240

Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
            260                 265                 270

Ser Asp Ser Glu Glu Gly Asp Asp Gln Gly Glu Lys Lys Arg
        275                 280                 285

Lys Gly Gly Arg Asn Phe Gln Thr Ala His Arg Arg Asn Met Leu Lys
    290                 295                 300

Gly Gln His Glu Lys Glu Ala Ala Asp Arg Lys Arg Lys Gln Glu Glu
```

```
                305                 310                 315                 320
Gln Met Glu Thr Glu Gln Gln Asn Lys Asp Glu Gly Lys Lys Pro Glu
                    325                 330                 335

Val Lys Lys Val Glu Lys Lys Arg Glu Thr Ser Met Asp Ser Arg Leu
                340                 345                 350

Gln Arg Ile His Ala Glu Ile Lys Asn Ser Leu Lys Ile Asp Asn Leu
            355                 360                 365

Asp Val Asn Arg Cys Ile Glu Ala Leu Asp Glu Leu Ala Ser Leu Gln
        370                 375                 380

Val Thr Met Gln Gln Ala Gln Lys His Thr Glu Met Ile Thr Thr Leu
385                 390                 395                 400

Lys Lys Ile Arg Arg Phe Lys Val Ser Gln Val Ile Met Glu Lys Ser
                405                 410                 415

Thr Met Leu Tyr Asn Lys Phe Lys Asn Met Phe Leu Val Gly Glu Gly
            420                 425                 430

Asp Ser Val Ile Thr Gln Val Leu Asn Lys Ser Leu Ala Glu Gln Arg
        435                 440                 445

Gln His Glu Glu Ala Asn Lys Thr Lys Asp Gln Gly Lys Lys Gly Pro
    450                 455                 460

Asn Lys Lys Leu Glu Lys Glu Gln Thr Gly Ser Lys Thr Leu Asn Gly
465                 470                 475                 480

Gly Ser Asp Ala Gln Asp Gly Asn Gln Pro Gln His Asn Gly Glu Ser
                485                 490                 495

Asn Glu Asp Ser Lys Asp Asn His Glu Ala Ser Thr Lys Lys Lys Pro
            500                 505                 510

Ser Ser Glu Glu Arg Glu Thr Glu Ile Ser Leu Lys Asp Ser Thr Leu
        515                 520                 525

Asp Asn
    530

<210> SEQ ID NO 26
<211> LENGTH: 333
<212> TYPE: PRT
<213> ORGANISM: Homo sapiens

<400> SEQUENCE: 26

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65              70                  75                  80

Leu Trp Glu Ile Asp Asn Asn Pro Lys Val Lys Phe Ser Ser Gln Gln
            85                  90                  95

Ala Ala Thr Lys Gln Ser Asn Ala Ser Ser Asp Val Glu Val Glu Glu
        100                 105                 110

Lys Glu Thr Ser Val Ser Lys Glu Asp Thr Asp His Glu Glu Lys Ala
    115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
```

```
                145                 150                 155                 160
Glu Ala Gly Val Val Thr Thr Ala Thr Ala Ser Val Asn Leu Lys Val
                    165                 170                 175

Ser Pro Lys Arg Gly Arg Pro Ala Ala Thr Glu Val Lys Ile Pro Lys
                180                 185                 190

Pro Arg Gly Arg Pro Lys Met Val Lys Gln Pro Cys Pro Ser Glu Ser
            195                 200                 205

Asp Ile Ile Thr Glu Glu Asp Lys Ser Lys Lys Gly Gln Glu Glu
        210                 215                 220

Lys Gln Pro Lys Lys Gln Pro Lys Lys Asp Glu Glu Gly Gln Lys Glu
225                 230                 235                 240

Glu Asp Lys Pro Arg Lys Glu Pro Asp Lys Lys Glu Gly Lys Lys Glu
                245                 250                 255

Val Glu Ser Lys Arg Lys Asn Leu Ala Lys Thr Gly Val Thr Ser Thr
                260                 265                 270

Ser Asp Ser Glu Glu Glu Gly Asp Asp Gln Gly Glu Lys Lys Arg
            275                 280                 285

Lys Gly Gly Arg Asn Phe Gln Thr Ala His Arg Arg Asn Met Leu Lys
            290                 295                 300

Gly Gln His Glu Lys Glu Ala Ala Asp Arg Lys Arg Lys Gln Glu Glu
305                 310                 315                 320

Gln Met Glu Thr Glu His Gln Thr Thr Cys Asn Leu Gln
                325                 330

<210> SEQ ID NO 27
<211> LENGTH: 530
<212> TYPE: PRT
<213> ORGANISM: Homo sapiens

<400> SEQUENCE: 27

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
                20                  25                  30

Val Lys Pro Pro Thr Asn Lys Leu Pro Ile Phe Phe Gly Thr His
            35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65              70                  75                  80

Leu Trp Glu Ile Asp Asn Asn Pro Lys Val Lys Phe Ser Ser Gln Gln
                85                  90                  95

Ala Ala Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
```

-continued

```
            195                 200                 205
Asp Ile Ile Thr Glu Glu Asp Lys Ser Lys Lys Gly Gln Glu Glu
        210                 215                 220
Lys Gln Pro Lys Lys Gln Pro Lys Lys Asp Glu Glu Gly Gln Lys Glu
225                 230                 235                 240
Glu Asp Lys Pro Arg Lys Glu Pro Asp Lys Lys Glu Gly Lys Lys Glu
                245                 250                 255
Val Glu Ser Lys Arg Lys Asn Leu Ala Lys Thr Gly Val Thr Ser Thr
            260                 265                 270
Ser Asp Ser Glu Glu Glu Gly Asp Asp Gln Glu Gly Glu Lys Lys Arg
            275                 280                 285
Lys Gly Gly Arg Asn Phe Gln Thr Ala His Arg Arg Asn Met Leu Lys
        290                 295                 300
Gly Gln His Glu Lys Glu Ala Ala Asp Arg Lys Arg Lys Gln Glu Glu
305                 310                 315                 320
Gln Met Glu Thr Glu Gln Gln Asn Lys Asp Glu Gly Lys Lys Pro Glu
                325                 330                 335
Val Lys Lys Val Glu Lys Lys Arg Glu Thr Ser Met Asp Ser Arg Leu
            340                 345                 350
Gln Arg Ile His Ala Glu Ile Lys Asn Ser Leu Lys Ile Asp Asn Leu
            355                 360                 365
Asp Val Asn Arg Cys Ile Glu Ala Leu Asp Glu Leu Ala Ser Leu Gln
        370                 375                 380
Val Thr Met Gln Gln Ala Gln Lys His Thr Glu Met Ile Thr Thr Leu
385                 390                 395                 400
Lys Lys Ile Arg Arg Phe Lys Val Ser Gln Val Ile Met Glu Lys Ser
                405                 410                 415
Thr Met Leu Tyr Asn Lys Phe Lys Asn Met Phe Leu Val Gly Glu Gly
            420                 425                 430
Asp Ser Val Ile Thr Gln Val Leu Asn Lys Ser Leu Ala Glu Gln Arg
            435                 440                 445
Gln His Glu Glu Ala Asn Lys Thr Lys Asp Gln Gly Lys Lys Gly Pro
        450                 455                 460
Asn Lys Lys Leu Glu Lys Glu Gln Thr Gly Ser Lys Thr Leu Asn Gly
465                 470                 475                 480
Gly Ser Asp Ala Gln Asp Gly Asn Gln Pro Gln His Asn Gly Glu Ser
                485                 490                 495
Asn Glu Asp Ser Lys Asp Asn His Glu Ala Ser Thr Lys Lys Lys Pro
            500                 505                 510
Ser Ser Glu Glu Arg Glu Thr Glu Ile Ser Leu Lys Asp Ser Thr Leu
            515                 520                 525
Asp Asn
530
```